(12) United States Patent
Tang et al.

(10) Patent No.: US 11,079,372 B2
(45) Date of Patent: Aug. 3, 2021

(54) POLYMERS AND CONJUGATES COMPRISING THE SAME

(71) Applicant: Ventana Medical Systems, Inc., Tucson, AZ (US)

(72) Inventors: Lei Tang, Oro Valley, AZ (US); Wenjun Zhang, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 171 days.

(21) Appl. No.: 15/476,904

(22) Filed: Mar. 31, 2017

(65) Prior Publication Data

US 2017/0205399 A1 Jul. 20, 2017

Related U.S. Application Data

(63) Continuation of application No. PCT/EP2015/072701, filed on Oct. 1, 2015.

(60) Provisional application No. 62/059,073, filed on Oct. 2, 2014, provisional application No. 62/212,879, filed on Sep. 1, 2015.

(51) Int. Cl.
*G01N 33/532* (2006.01)
*G01N 33/533* (2006.01)

(52) U.S. Cl.
CPC ......... *G01N 33/533* (2013.01); *G01N 33/532* (2013.01); *G01N 2458/10* (2013.01)

(58) Field of Classification Search
CPC . G01N 33/532; G01N 33/533; G01N 2458/10
See application file for complete search history.

(56) References Cited

U.S. PATENT DOCUMENTS

| | | | |
|---|---|---|---|
| 4,824,775 A | 4/1989 | Dattagupta | |
| 5,547,860 A | 8/1996 | Koecher | |
| 5,641,629 A | 6/1997 | Pitner | |
| 7,309,567 B1 | 12/2007 | Mathis et al. | |
| 7,428,957 B2 | 9/2008 | Schaefer | |
| 7,842,175 B2 * | 11/2010 | Kawabata | C12Q 1/68 204/450 |
| 2004/0198971 A1 | 10/2004 | Rabbani | |
| 2010/0203516 A1 | 8/2010 | Campbell et al. | |
| 2010/0248980 A1 | 9/2010 | Park et al. | |

(Continued)

FOREIGN PATENT DOCUMENTS

| | | |
|---|---|---|
| EP | 1376126 A1 | 1/2004 |
| EP | 1489422 A2 | 12/2004 |
| EP | 2444807 A2 | 4/2012 |

(Continued)

OTHER PUBLICATIONS

Flor et al. DNA-directed assembly of antibody-fluorophore conjugates for quantitative multiparametric flow cytometry. Chembiochem 2014, vol. 15, No. 2, pp. 267-275. (Year: 2014).*

(Continued)

*Primary Examiner* — Shafiqul Haq
(74) *Attorney, Agent, or Firm* — Charney IP Law LLC; Thomas M. Finetti

(57) ABSTRACT

Polymers and conjugates comprising polymers are disclosed herein. In some embodiments, the conjugates disclosed are suitable for use as detection probes in immunohistochemical assays, including multiplex immunohistochemical assays.

27 Claims, 17 Drawing Sheets
(8 of 17 Drawing Sheet(s) Filed in Color)

Specification includes a Sequence Listing.

(56) References Cited

U.S. PATENT DOCUMENTS

| | | |
|---|---|---|
| 2011/0311966 A1 | 12/2011 | Hennig |
| 2013/0196880 A1 | 8/2013 | Stanislaw et al. |

FOREIGN PATENT DOCUMENTS

| | | |
|---|---|---|
| EP | 2865762 A1 | 4/2015 |
| JP | 2002539453 | 11/2002 |
| JP | 2004309486 A | 11/2004 |
| JP | 2008-82784 A | 4/2008 |
| JP | 4214779 B2 | 11/2008 |
| JP | 2010-528285 A | 8/2010 |
| WO | 9705156 A1 | 2/1997 |
| WO | 99/43287 A2 | 9/1999 |
| WO | 2008153744 A2 | 12/2008 |
| WO | WO2009112032 A1 | 9/2009 |
| WO | WO2013191265 A1 | 12/2013 |
| WO | 2015124702 A1 | 8/2015 |

OTHER PUBLICATIONS

Gzybowski et al. Synthesis and antibody-mediated detection of oligonucleotides containing multiple 2,4-dinitrophenyl reporter groups. Nucleic Acids Res. 1993, vol. 21, pp. 1705-1712. (Year: 1993).*

Kozlov et al. Efficient Strategies for the conjugation of oligonucleotides to antibodies enabling highly sensitive protein detection. Biopolymers, vol. 73, pp. 621-630. (Year: 2003).*

Giusti et al. Synthesis and characterization of 5'-fluorescent-dye-labeled oligonucleotides. Genome Res. 1993, pp. 223-227 (Year: 1993).*

Dohmen et al. Defined folate-peg-siRNA conjugates for receptor-specific gene silencing. Molecular Therapy-Nucleic Acids 2012, pp. 1-6. (Year: 2012).*

Milton et al. Efficient self-assembly of DNA-functionalized fluorophores and gold nanoparticles with DNA functionalized silicon surfaces: the effect of oligomer spacers. Nucleic Acids Research, 2013, vol. 41, No. 7, pp. 1-12 (Year: 2013).*

Tyagi et al. Fluorescence spectroscopic behavior of floic acid. Chemical Physics 2010, vol. 367, pp. 83-92. (Year: 2010).*

Lu et al. A simple and sensitive assay for the determination of nitrite using folic acid as the fluorescent probe. Anal. Methods 2015, vol. 7, pp. 1543-1548 (Year: 2015).*

European search report dated Sep. 20, 2018 in corresponding EP application No. 15777651.9.

Grzybowski, J., et al., Synthesis and antibody-mediated detection of oligonucleotides containing multiple 2,4-dinitrophenyl reporter groups, Nucl Acids Res, 1993, 1705-1712, 21.

International Preliminary Report on Patentability dated Apr. 4, 2017 in corresponding PCT/EP2015/072701, pp. 1-11.

International Search Report and Written Opinion dated Apr. 4, 2016 in corresponding PCT/EP20151072701, pp. 1-18.

Ishikawa, E., Immunomicroassay Method for Macromolecule Antigens, Chemistry and Biology, (1985), pp. 386-393, vol. 23.

Manabe, Linker Technology in Antibody-Drug Conjugates for Cancer Treatment, Drug Delivery System, (2013), pp. 406-411, vol. 28.

Nakamura, T., Development of Chemical Modification Method for Terminals and Interiors of DNA and RNA, Biochemistry, (2010), pp. 1141-1145, vol. 82.

* cited by examiner

5'-(AminoC6)-TA[Sp~C18][DNP]TA[Sp~C18][DNP]TA[Sp~C18][DNP]
TA[Sp~C18][DNP]TA[Sp~C18][DNP]TA[Sp~C18][DNP]TA[Sp~C18][DNP]
TA[Sp~C18][DNP]TA[Sp~C18][DNP]T -3'

CD3

1µg/ml native CD3, GaR-HRP

1µg/ml CD3-18mer-9DNP, Ms anti-DNP-HRP

The staining similar to the bottom left suggests the major portion is conjugated Ab-Oligo complex, not the unconjugated Ab 1µg/ml CD3-18mer-9DNP, GaR-HRP

CD20

1μg/ml native CD20, GaR-HRP

1μg/ml CD20-18mer-9DNP, Ms anti-DNP-HRP

The staining similar to the bottom left suggests the major portion is conjugated Ab-Oligo complex, not the unconjugated Ab 1μg/ml CD20-18mer-9DNP, GaR-HRP

CD68

Note: CD68 antibody amino acid sequence analysis suggests potential disulfide bond formation in CDR3

1μg/ml native CD68, GaR-HRP

1μg/ml CD68-18mer-9DNP, Ms anti-DNP-HRP

The staining similar to the bottom left suggests the major portion is conjugated Ab-Oligo complex, not the unconjugated Ab 1μg/ml CD68-18mer-9DNP, GaR-HRP FoxP3                                        FIG. 15
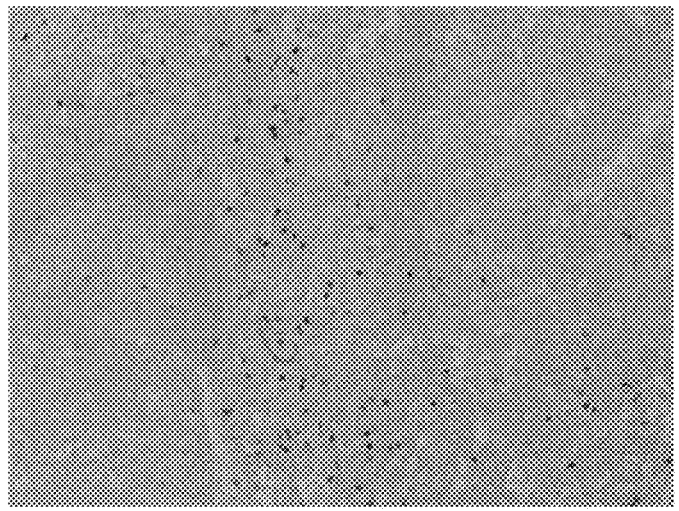
Note: FoxP3 antibody amino acid sequence analysis suggests potential disulfide bond formation in CDR3
1μg/ml native FoxP3, GaR-HRP
1μg/ml FoxP3-18mer-9DNP, Ms anti-DNP-HRP
The staining similar to the bottom left suggests the major portion is conjugated Ab-Oligo complex, not the unconjugated Ab
1μg/ml FoxP3-18mer-9DNP, GaR-HRP CD8                                                     FIG. 16
1μg/ml native CD8, GaR-HRP
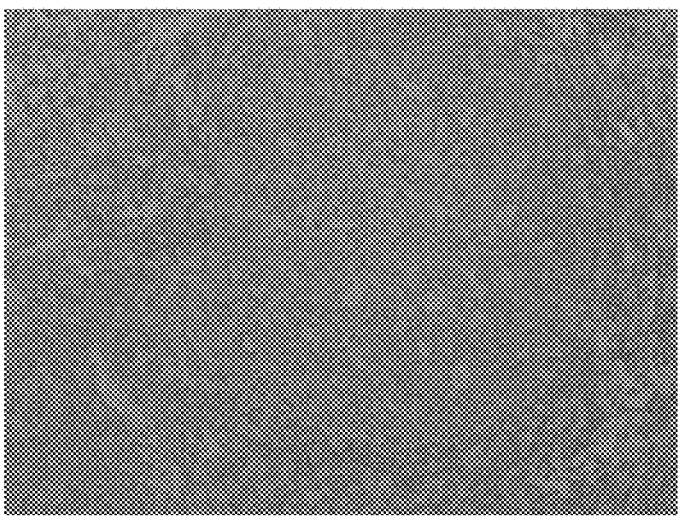
1μg/ml CD8-18mer-9DNP, Ms anti-DNP-HRP
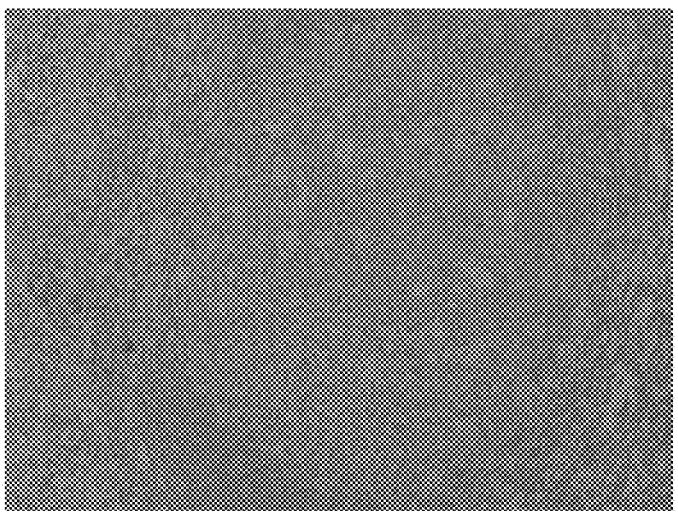
1μg/ml CD8-18mer-9DNP, GaR-HRP

POLYMERS AND CONJUGATES COMPRISING THE SAME

CROSS REFERENCE TO RELATED APPLICATIONS

This patent application is a continuation of International Patent Application No. PCT/EP2015/072701 filed Oct. 1, 2015, which claims priority to and the benefit of U.S. Provisional Patent Application No. 62/059,073 filed Oct. 2, 2014, and U.S. Provisional Patent Application No. 62/212,879, filed Sep. 1, 2015. Each of the above patent applications is incorporated herein by reference as if set forth in its entirety.

Cell staining methods, including immunohistochemistry (IHC) and in situ hybridization analysis (ISH), are useful tools in histological diagnosis and the study of tissue morphology. IHC employs specific binding agents or moieties, such as antibodies, to detect an antigen of interest that may be present in a tissue sample. IHC is widely used in clinical and diagnostic applications, such as to diagnose particular disease states or conditions. For example, particular cancer types can be diagnosed based on the presence of a particular marker molecule in a sample obtained from a subject. IHC is also widely used in basic research to understand biomarker distribution and localization in different tissues. Biological samples also can be examined using in situ hybridization techniques, such as silver in situ hybridization (SISH), chromogenic in situ hybridization (CISH) and fluorescence in situ hybridization (FISH), collectively referred to as ISH. ISH is distinct from IHC, in that ISH detects nucleic acids in tissue whereas IHC detects proteins.

Characterization and quantitation of the multitude of proteins expressed by an organism's genome are the focus of proteomics. Multiplex immunohistochemistry (MIHC) represents a major unmet technological need to detect and analyze multivariate protein targets in paraffin-embedded formalin-fixed tissues with broad applications in research and diagnostics. Multiplex immunohistochemistry (MIHC) techniques are attempting to address the need for detecting and analyzing multivariate protein targets in formalin-fixed, paraffin-embedded tissues. Effective MIHC techniques have broad applications in research and diagnostics. However, there are few, if any, efficient and reproducible methods that allow simultaneous and quantitative detection of multiple (e.g. >=5) 25 protein targets in tissues.

For in situ assays such as IHC assays and ISH assays of tissue and cytological samples, especially multiplexed assays of such samples, it is highly desirable to identify and develop methods which provide desirable results without background interference. One such method involves the use of Tyramide Signal Amplification (TSA), which is based on the patented catalyzed reporter deposition (CARD). U.S. Pat. No. 6,593,100, entitled "Enhanced catalyzed reporter deposition" discloses enhancing the catalysis of an enzyme in a CARD or TSA method by reacting a labeled phenol conjugate with an enzyme, wherein the reaction is carried out in the presence of an enhancing reagent.

Biomolecular conjugate immunoassays are useful for detecting specific target molecules in a sample. Ventana Medical Systems, Inc. is the assignee of a number of patents and applications in this general area, including: U.S. patent application Ser. No. 11/603,425, entitled "Molecular Conjugate"; U.S. utility application Ser. No. 11/982,627, entitled "Haptens, Hapten Conjugates, Compositions Thereof and Method for their Preparation and Use"; and U.S. Pat. No. 8,486,620, entitled Polymeric Carriers for Immunohistochemistry and in situ hybridization. Each of these prior applications and patents is incorporated herein by reference. Haptens and corresponding hapten-carrier conjugates have been essential to the development of sensitive quantitative and qualitative immunoassays. In the design of hapten conjugates, consideration must be given to the hapten, the carrier, the coupling strategy, and the hapten density because the amount of hapten attached to the carrier may influence the strength of the response directed toward the newly created antigenic determinant. It is believed, however, that certain conjugates may interfere with the assay, such as through steric effects, deactivation of reactive functional groups critical for appropriate functioning, changes in solubility, background noise, etc.

BRIEF SUMMARY OF THE INVENTION

In one aspect of the present disclosure is a polymer of Formula (V),

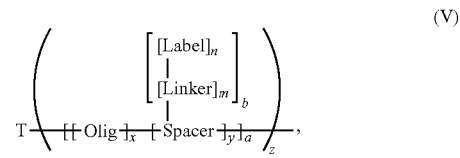

wherein 'Olig' is an oligonucleotide sequence having between 1 and about 50 nucleotides, wherein the oligonucleotide sequence has a Tm of less than 70° C.; 'Spacer' is a branched or unbranched, substituted or unsubstituted, saturated or unsaturated aliphatic group, optionally having one or more heteroatoms selected from O, N, or S, and having between 4 and 32 carbon atoms; 'Linker' is a branched or unbranched, substituted or unsubstituted, saturated or unsaturated aliphatic group, optionally having one or more heteroatoms selected from O, N, or S, and having between 4 and 18 carbon atoms; 'Label' is selected from the group consisting of haptens, fluorophores, chromogens, enzymes and quantum dots; R is a terminal group (non-limiting examples include hydrogen, a hydroxyl group, a carbonyl group, an amino group, a phosphate group, a phosphodiester group, or a cation); T is a group having a terminal reactive moiety; x is 1 or 2; y is 0, 1, or 2; z is an integer ranging from 1 to 18; m is 0, 1, or 2; n is 1 or 2; a is an integer ranging from 1 to 8; b is 1 or 2; wherein any of the 'Olig,' Spacer, "Linker," or 'Label' may be bonded directly to each other or through an optional group (e.g. phosphate group or phosphodiester group); and wherein when y is 0, [Spacer] is a bond; and when m is 0, [Linker] is a bond. In some embodiments of the polymer of Formula (V), the terminal reactive moiety of T is an amino group, a carboxyl group, or a sulfhydryl group, or other group which may couple to a specific binding entity. In some embodiments, the 'Olig' comprises between 2 and about 50 nucleotides. In some embodiments, the 'Olig' comprises between 2 and about 24 nucleotides. In some embodiments, the 'Olig' comprises between 4 and about 24 nucleotides; x is 1; y is 1; and a is 1 or 2. In embodiments where y is zero and [Spacer] is a bond, the [Linker], if present, is coupled or bonded to the [Olig], either directly or through an optional group (e.g. phosphate group or phosphodiester group). In embodiments where m is zero and [Linker] is a bond, the [Label] is coupled or bonded to the [Spacer], either directly or through an optional group (e.g. phosphate group or phosphodiester group). In embodiments where y is zero and m is zero, the [Label] is bonded to the [Olig], either directly or through an optional group (e.g. phosphate group or phosphodiester group).

In some embodiments, the 'Spacer' has the structure of Formula (VII)

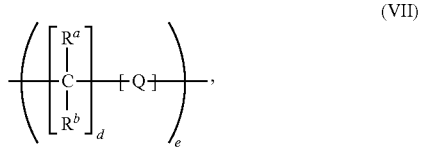

wherein d and e are integers ranging from 1 to 32; Q is a bond, O, S, or $N(R^c)(R^d)$; $R^a$ and $R^b$ are independently H, a $C_1$-$C_4$ alkyl group, F, Cl, $N(R^c)(R^d)$; and $R^c$ and $R^d$ are independently $CH_3$ or H. In some embodiments, $R^a$ and $R^b$ are H; Q is O; d ranges from 1 to 4; and e ranges from 2 to 8. In some embodiments, $R^a$ and $R^b$ are H; Q is O; d is 2; and e ranges from 2 to 8. In some embodiments, the 'Spacer' has a net positive charge.

In some embodiments, the 'Linker' has the structure of Formula (VII),

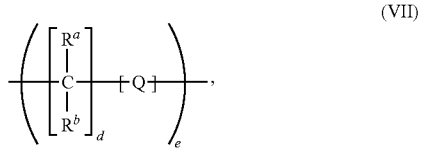

wherein d and e are integers ranging from 1 to 32; Q is a bond, O, S, or $N(R^c)(R^d)$; $R^a$ and $R^b$ are independently H, a $C_1$-$C_4$ alkyl group, F, Cl, $N(R^c)(R^d)$; and $R^C$ and $R^d$ are independently $CH_3$ or H. In some embodiments, the 'Linker' is derived from a poly(alkylene)glycol.

In some embodiments, 'Label' is selected from the group consisting of di-nitrophenyl, biotin, digoxigenin, fluorescein or a derivative thereof, or rhodamine. In some embodiments, the 'Label' is selected from the group consisting of oxazoles, pyrazoles, thiazoles, nitroaryls, benzofurans, triterpenes, ureas, thioureas, rotenoids, coumarins, or cyclolignans. In other embodiments, 'Label' is selected from the group consisting of 5-nitro-3-pyrazole carbamide, 2-(3,4-dimethoxyphenyl)quinoline-4-carboxylic acid), 3-hydroxy-2-quinoxalinecarbamide, 2,1,3-benzoxadiazole-5-carbamide, and 2-acetamido-4-methyl-5-thiazolesulfonamide.

In other embodiments of the polymer of Formula (V), x is 1; y is 1 or 2; a is 1 or 2; and z ranges from between 3 to 18. In some embodiments, x is 1; y is 1; a is 1 or 2; and z ranges from between 3 to 9. In some embodiments, a is 2; and m, n, and b are 1. In some embodiments, 'Label' is fluorescein. In some embodiments, 'Olig' comprises between 4 and 18 nucleotides; and wherein 'Linker' comprises between 4 and 12 carbon atoms.

In yet other embodiments of the polymer of Formula (V), x is 1; y is 1; a is 1; and m, n, and b are 1. In some embodiments, the 'Label' is di-nitrophenyl. In some embodiments, 'Olig' comprises between 4 and 18 nucleotides; and wherein 'Linker' comprises between 4 and 12 carbon atoms.

In some embodiments of the polymer of Formula (V), x is 1; y is 0; a is 1 or 2; and z ranges from between 3 to 9.

In some embodiments, the 'Label' is di-nitrophenyl. In some embodiments, 'Olig' comprises between 4 and 18 nucleotides; and wherein 'Linker' comprises between 4 and 12 carbon atoms.

In some embodiments of the polymer of Formula (V), a ratio of a:b is 2:1 or 3:1; and wherein a number of 'Label' groups per polymer ranges from 3 to 9.

In another aspect of the present disclosure is a composition comprising a target-specific antibody having between about 2 to about 4 polymers coupled thereto, wherein each polymer comprises plural labels, and wherein a number of detectable labels per target-specific antibody is at least 6. In some embodiments, each polymer comprises between 3 to 18 detectable Labels. In some embodiments, the polymer has the structure of Formula (V)

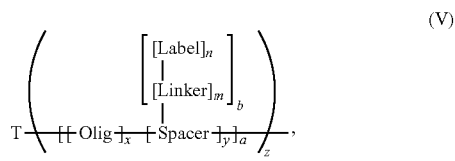

wherein 'Olig' is a single-stranded oligonucleotide sequence having between 1 and about 32 nucleotides, wherein the oligonucleotide sequence has a Tm of less than 70° C.; 'Spacer' is a branched or unbranched, substituted or unsubstituted, saturated or unsaturated aliphatic group, optionally having one or more heteroatoms selected from O, N, or S, and having between 4 and 24 carbon atoms; 'Linker' is an aliphatic group, optionally having one or more heteroatoms selected from O, N, or 5, and having between 4 and 18 carbon atoms; 'Label' is selected from the group consisting of haptens, fluorophores, and quantum dots; R is a terminal group (non-limiting examples include hydrogen, a hydroxyl group, a carbonyl group, an amino group, a phosphate group, a phosphodiester group, or a cation); T is a group having a terminal reactive moiety which may couple to an antibody; x is 1 or 2; y is 0, 1, or 2; m is 0, 1, or 2; n is 1 or 2; z is an integer ranging from 1 to 18; a is an integer ranging from 1 to 8; b is 1 or 2; wherein any of the 'Olig', 'Spacer,' or 'Linker' may be bonded directly to each other or through an optional group (e.g. a phosphate group or phosphodiester group), and wherein when y is 0, [Spacer] is a bond; and when m is 0, [Linker] is a bond. In embodiments where y is zero and [Spacer] is a bond, the [Linker], if present, is coupled or bonded to the [Olig], either directly or through an optional group (e.g. phosphate group or phosphodiester group). In embodiments where m is zero and [Linker] is a bond, the [Label] is coupled or bonded to the [Spacer], either directly or through an optional group (e.g. phosphate group or phosphodiester group). In embodiments where y is zero and m is zero, the [Label] is bonded to the [Olig], either directly or through an optional group (e.g. phosphate group or phosphodiester group).

In some embodiments, the 'Spacer' or [Spacer], has a net positive charge. In some embodiments, a distance between successive 'Labels' in each polymer is less than about 10 nm. In some embodiments, at least four carbon atoms or a combination of four carbon atoms and heteroatoms of any 'Spacer' comprises part of the polymeric backbone.

In some embodiments, the composition comprises the polymer of Formula (V) where x is 1; y is 1; a is 1 or 2; z ranges from between 3 to 9; the 'Label' is fluorescein (or a fluorescein derivative); 'Olig' comprises between 4 and 18 nucleotides; and 'Linker' comprises between 4 and 12 carbon atoms. In some embodiments, a is 2.

In other embodiments, the composition comprises the polymer of Formula (V) where x is 1; y is 1; a is 1 or 2; z ranges from between 3 to 9; the 'Label' is di-nitrophenyl; 'Olig' comprises between 4 and 18 nucleotides; and 'Linker' comprises between 4 and 12 carbon atoms. In some embodiments, a is 1.

In another aspect of the present disclosure is a method for detecting multiple targets in a sample, comprising: contacting a formalin fixed paraffin embedded sample (e.g. a tissue sample) with two or more different conjugates according to Formula (VId),

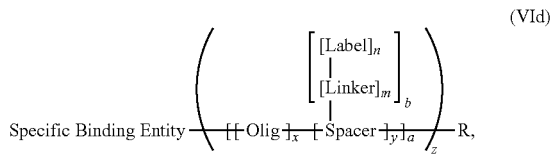

wherein 'Olig' is a single-stranded oligonucleotide sequence having between 1 and about 32 nucleotides, wherein the oligonucleotide sequence has a Tm of less than 70° C.; 'Spacer' is a branched or unbranched, substituted or unsubstituted, saturated or unsaturated aliphatic group, optionally having one or more heteroatoms selected from O, N, or S, and having between 4 and 24 carbon atoms; 'Linker' is an aliphatic group, optionally having one or more heteroatoms selected from O, N, or S, and having between 4 and 18 carbon atoms; 'Label' is selected from the group consisting of haptens, fluorophores, and quantum dots; 'Specific Binding Entity" is an antibody, antibody fragment, nucleic acid, or drug/antibody conjugate; R is a terminal group (non-limiting examples include hydrogen, a hydroxyl group, an amino group, a carbonyl group, a phosphate group, a phosphodiester group, or a cation); x is 1 or 2; y is 0, 1, or 2; m is 0, 1, or 2; n is 1 or 2; a is an integer ranging from 1 to 18; a is an integer ranging from 1 to 8; b is an integer ranging from 1 to 8; and wherein any of the 'Olig', 'Spacer,' or 'Linker' may be bonded directly to each other or through an optional group; wherein when y is 0, [Spacer] is a bond; and when m is 0, [Linker] is a bond, wherein each of the different conjugates bind specifically to different targets within the sample and wherein each of the conjugates comprise different Labels; contacting the sample with detection reagents specific to the label of the different antibody conjugates and wherein each detection reagent comprises a different detectable moiety; and detecting the multiple targets using the different detectable moieties. In some embodiments, detectable moieties of the detection reagents are selected from the group consisting of organic dyes, fluorophores, enzymes, quantum dots, or haptens. In some embodiments, amounts of different targets within the sample are quantified based on signal output from the detectable labels. In some embodiments, the method further comprises the step of scoring the sample based on the quantified targets.

In embodiments where y is zero and [Spacer] is a bond, the [Linker], if present, is coupled or bonded to the [Olig], either directly or through an optional group (e.g. phosphate group or phosphodiester group). In embodiments where m is zero and [Linker] is a bond, the [Label] is coupled or bonded to the [Spacer], either directly or through an optional group (e.g. phosphate group or phosphodiester group). In embodiments where y is zero and m is zero, the [Label] is bonded to the [Olig], either directly or through an optional group (e.g. phosphate group or phosphodiester group).

In another aspect of the present disclosure is a conjugate of Formula (VId):

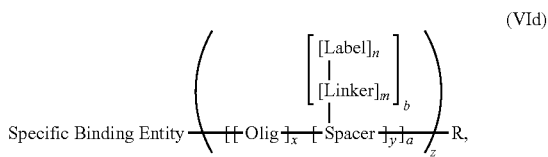

wherein 'Olig' is a single-stranded oligonucleotide sequence having between 1 and about 32 nucleotides, wherein the oligonucleotide sequence has a Tm of less than 70° C.; 'Spacer' is a branched or unbranched, substituted or unsubstituted, saturated or unsaturated aliphatic group, optionally having one or more heteroatoms selected from O, N, or S, and having between 4 and 24 carbon atoms; 'Linker' is an aliphatic group, optionally having one or more heteroatoms selected from O, N, or S, and having between 4 and 18 carbon atoms; 'Label' is selected from the group consisting of haptens, fluorophores, and quantum dots; 'Specific Binding Entity" is an antibody, antibody fragment, nucleic acid, or drug/antibody conjugate; R is a terminal group (non-limiting examples include hydrogen, a hydroxyl group, a carbonyl group, an amino group, a phosphate group, a phosphodiester group, or a cation); x is 1 or 2; y is 0, 1, or 2; m is 0, 1, or 2; n is 1 or 2; a is an integer ranging from 1 to 8; b is 1 or 2; z is an integer ranging from 1 to 18; and wherein any of the 'Olig', 'Spacer,' or 'Linker' may be bonded directly to each other or through an optional group, and wherein when y is 0, [Spacer] is a bond; and when m is 0, [Linker] is a bond. In embodiments where y is zero and [Spacer] is a bond, the [Linker], if present, is coupled or bonded to the [Olig], either directly or through an optional group (e.g. phosphate group or phosphodiester group). In embodiments where m is zero and [Linker] is a bond, the [Label] is coupled or bonded to the [Spacer], either directly or through an optional group (e.g. phosphate group or phosphodiester group). In embodiments where y is zero and m is zero, the [Label] is bonded to the [Olig], either directly or through an optional group (e.g. phosphate group or phosphodiester group). In some embodiments, at least four carbon atoms or a combination of four carbon atoms and heteroatoms of any 'Spacer' comprises part of the polymeric backbone.

In some embodiments, the Specific Binding Entity is an Antibody, a nucleic acid, or a drug/antibody complex/conjugate. In some embodiments, the Specific Binding Entity is an Antibody. In some embodiments, the 'Olig' comprises between 2 and about 50 nucleotides. In some embodiments, 'Olig' comprises between 2 and about 24 nucleotides. In some embodiments, the 'Olig' comprises between 4 and about 24 nucleotides; x is 1; y is 1; and a is 1 or 2.

In some embodiments, the 'Spacer' has the structure of Formula (VII)

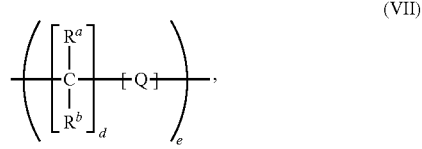

wherein d and e are integers ranging from 1 to 32; Q is a bond, 0, 5, or N(R$^c$)(R$^d$); R$^a$ and R$^b$ are independently H, a C$_1$-C$_4$ alkyl group, F, Cl, N(R$^c$)(R$^d$); and R$^c$ and R$^d$ are independently CH$_3$ or H. In some embodiments, Ra and Rb are H; Q is O; d ranges from 1 to 4; and e ranges from 2 to 8. In some embodiments, R$^a$ and R$^b$ are H; Q is O; d is 2; and e ranges from 2 to 8. In some embodiments, the 'Spacer' has a net positive charge.

In some embodiments, the 'Linker' has the structure of Formula (VII),

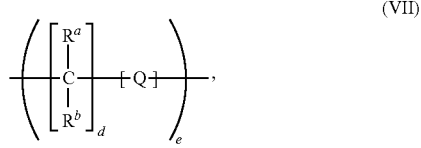

(VII)

wherein d and e are integers ranging from 1 to 32; Q is a bond, O, S, or N(R$^c$)(R$^d$); R$^a$ and R$^b$ are independently H, a C$_1$-C$_4$ alkyl group, F, Cl, N(R$^c$)(R$^d$); and R$^c$ and R$^d$ are independently CH$_3$ or H. In some embodiments, the 'Linker' is derived from a poly(alkylene)glycol.

In some embodiments, the 'Label' is selected from the group consisting of di-nitrophenyl, biotin, digoxigenin, fluorescein or a derivative thereof, or rhodamine. In other embodiments, the 'Label' is selected from the group consisting of oxazoles, pyrazoles, thiazoles, nitroaryls, benzofurans, triterpenes, ureas, thioureas, rotenoids, coumarins, or cyclolignans. In other embodiments, the 'Label' is selected from the group consisting of 5-nitro-3-pyrazole carbamide, 2-(3,4-dimethoxyphenyl)quinoline-4-carboxylic acid), 3-hydroxy-2-quinoxalinecarbamide, 2,1,3-benzoxadiazole-5-carbamide, and 2-acetamido-4-methyl-5-thiazolesulfonamide.

In some embodiments of the conjugate of Formula (VId), x is 1; y is 1 or 2; a is 1 or 2; and z ranges from between 3 to 18. In some embodiments, x is 1; y is 1; a is 1 or 2; and z ranges from between 3 to 9. In some embodiments, a is 2; and m, n, and b are 1. In some embodiments, the 'Label' is fluorescein (or a fluorescein derivative). In some embodiments, 'Olig' comprises between 4 and 18 nucleotides; and wherein 'Linker' comprises between 4 and 12 carbon atoms.

In other embodiments of the conjugate of Formula (VId), x is 1; y is 1 or 2; a is 1; and m, n, and b are 1. In some embodiments, the 'Label' is di-nitrophenyl. In some embodiments, 'Olig' comprises between 4 and 18 nucleotides; and wherein 'Linker' comprises between 4 and 12 carbon atoms.

In other embodiments of the conjugate of Formula (VId), x is 1; y is 0; a is 1 or 2; and z ranges from between 3 to 9. In some embodiments, 'Label' is di-nitrophenyl. In some embodiments, 'Olig' comprises between 4 and 18 nucleotides; and wherein 'Linker' comprises between 4 and 12 carbon atoms.

In other embodiments of the conjugate of Formula (VId), a ratio of a:b is 2:1 or 3:1; and wherein a number of 'Label' groups present per polymer ranges from 3 to 9.

In another aspect of the present disclosure is a conjugate of Formula (IVb),

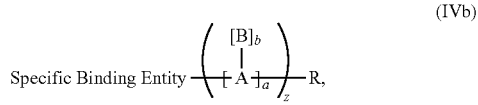

(IVb)

wherein the conjugate comprises at least two polymers of Formula (I),

(I)

wherein [A] is a polymer backbone comprising an oligonucleotide sequence and an optional spacer; [B] comprises a Label attached to the polymer backbone either directly or through an optional linker; a is an integer which ranges from 1 to 8; b is an integer that ranges from 1 to 8; z is an integer that ranges from 1 to 24; R is hydrogen, a hydroxyl group, an amino group, a carbonyl group, a phosphate group, a phosphodiester group, or a cation; and the Specific Binding Entity is an antibody, an antibody fragment, a nucleic acid, or a drug/antibody complex/conjugate. In some embodiments, a length or size of [A] ranges from between about 8 nm to about 12 nm. In some embodiments, the length or size is less than about 10 nm. In some embodiments, a is 1 or 2, b is 1 or 2, and z is an integer selected from 3, 4, 5, or 9. In some embodiments, a ratio of a:b is 1:1. In other embodiments, a ratio of a:b is 2:1. In yet other embodiments, a ratio of a:b is 3:1. In some embodiments, the number of polymers per specific binding entity ranges from about 2 to about 5. In other embodiments, the number of polymers per specific binding entity ranges from about 2 to about 4. In some embodiments, the constituent components of [A] and the number of times [A] is repeated relative to [B] are optimized such that Labels attached to the backbone are spaced a distance apart from each other that approximates the distance between antigen binding sites of a secondary antibody, where the secondary antibody is an anti-Label antibody.

In another aspect of the present disclosure is a method or automated method of performing a multiplexed diagnostic assay for multiple targets in a sample. This embodiment typically comprises providing a formalin-fixed, paraffin-embedded tissue sample; preparing the tissue sample for a multiplexed target analysis using an automated system; contacting the sample with multiple conjugates each having Formula (VId) that bind specifically to the multiple different targets using the automated system, wherein the each of the polymers constituting the conjugates have a plurality of Labels; contacting the sample with detection reagents for detecting the Labels of each of the conjugates using the automated system, where each of the detection reagents comprise a different detectable moiety; and detecting the targets using the detectable labels.

In another aspect of the present disclosure, are kits comprising at least one conjugate of Formula (IV) and detection reagents for detecting the at least one conjugate. In some embodiments, the kits comprise additional reagents, such as buffers.

While haptenylated primary antibodies are attractive reagents in multiplex IHC assays, Applicants have often observed weaker IHC staining with anti-hapten antibodies as compared with anti-species antibody staining. Similarly, direct fluorochrome labeled primary antibody staining is usually weaker than indirect IHC staining with an anti-species antibody. Given this, it is often necessary to increase the degree of labeling at the cost of reducing antibody activity.

Applicants have developed conjugates and compositions comprising conjugates which provide for a relatively low degree of labeling per specific binding entity to prevent deleterious effects on antibody activity (e.g. interference with the structure and binding affinity of the antibody to the target). In addition, Applicants have discovered that the use of the polymers as carriers for labels, especially those whose polymeric backbones are of a controlled size, length, spatial conformation, or electronic configuration, allows the labels to be separated from each other such that detection sensitivity is maximized (e.g. prevention or mitigation of steric hindrance of detection reagents). Overall, Applicants have discovered novel polymers that serve as carriers for labels, where the polymers are configured to comprise (i) oligonucleotides having a certain length or size; (ii) a precise number of labels; (iii) the optional incorporate of spacers between labels; and (iv) a pre-defined distance between labels. brief description of the drawings

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Non-limiting and non-exhaustive embodiments are described with reference to the following drawings. The same reference numerals refer to like parts or acts throughout the various views, unless otherwise specified.

FIGS. 12, 13, 14, 15, and 16 compare the results of IHC staining assays, where native antibodies and antibody conjugates according to the present disclosure are used.

Figure 1:
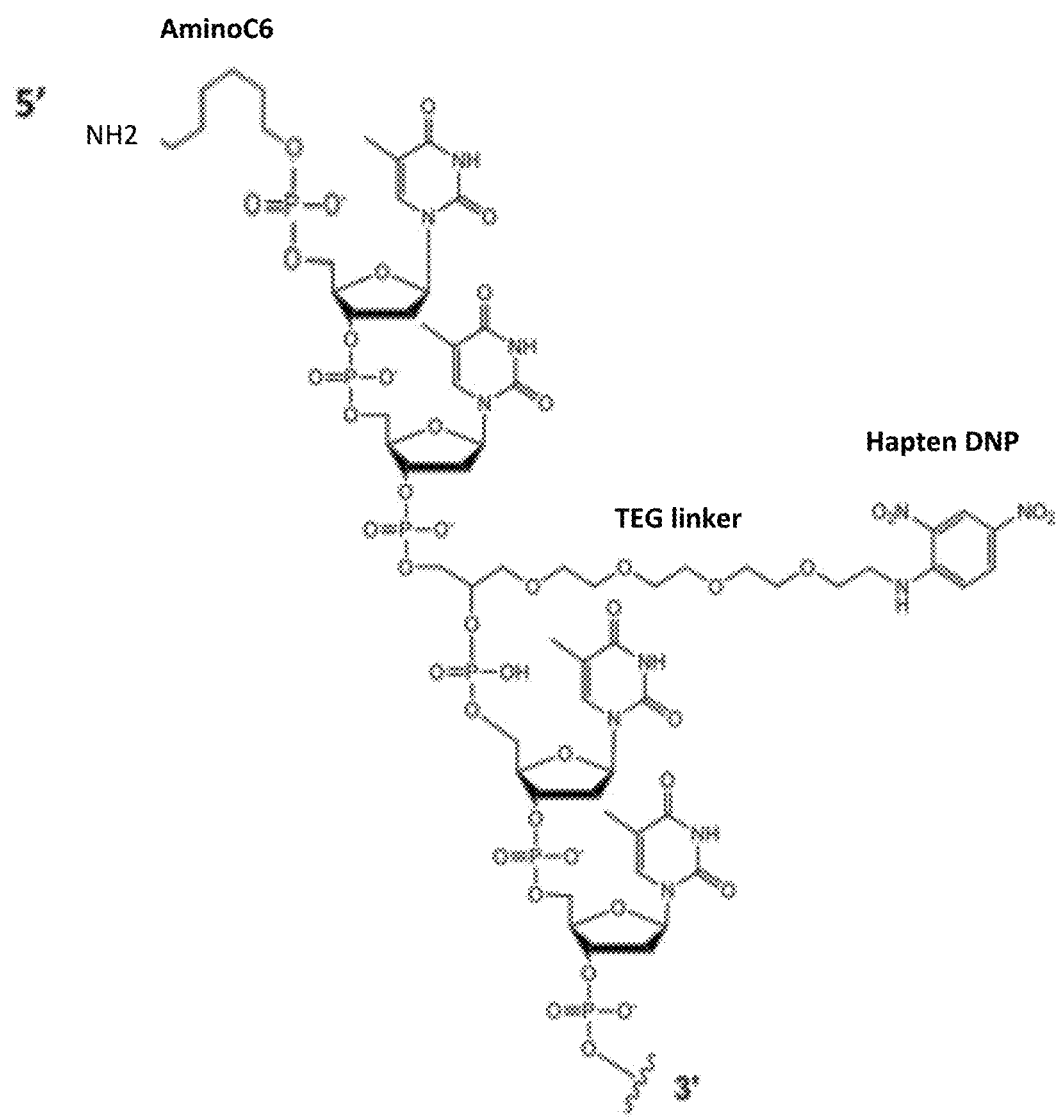
FIG. 1 illustrates an example of an antibody conjugate comprising an oligonucleotide polymer backbone and a label attached to the polymer backbone through a linker.

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "Ventana-028US2_P32365-US-2_ST25.txt" created on Apr. 23, 2021 3 KB, which is incorporated by reference herein.

DETAILED DESCRIPTION

In general, the present disclosure is directed to conjugates and compositions comprising conjugates as well as methods of employing those conjugates for detecting one or more targets present in a biological sample. In some embodiments, the conjugates or compositions are used in a multiplex assay to detect multiple targets within a tissue sample, either simultaneously or sequentially, while preventing deleterious effects on antibody activity.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Affimers™ are engineered proteins that mimic the specificity and binding affinities of antibodies, but are much smaller and have a molecular weight of about 14 kDa. They are believed to be highly stable and engineered to display peptide loops which provide a high affinity binding surface for a specific target protein.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')2, and Fv fragments; diabodies; linear antibodies; single-chain antibody molecules, e.g., sc-Fv; nanobodies and multispecific antibodies formed from antibody fragments.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins.

As used herein, the term "assay" includes, but is not limited to, singleplex and multiplex immundetection assays, such as immunohistochemistry (IHC), flow cytometry, microscopy, imaging, high content screening (HCS), immunocytochemistry (ICC), immunomagnetic cellular depletion, immunomagnetic cell capture, in situ hybridization (ISH), enzyme immuno-assay (EIA), enzyme linked immuno-assay (ELISA), ELISpot, arrays including bead arrays, multiplex bead array, microarray, antibody array, cellular array, solution phase capture, chemiluminescence detection, infrared detection, blotting method, a Western blot, a Southern blot, a Southwestern blot, labeling inside an electrophoresis system, labeling on a surface, labeling on an array, PCR amplification, elongation followed by PCR amplification, immunoprecipitation, coimmunoprecipitation, chromatin immunoprecipitation, pretargeting imaging, therapeutic agent, or combinations thereof.

As used herein, "conjugate" refers to two or more molecules (and/or materials such as nanoparticles) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules, such as one or more other biomolecules. In other embodiments, a conjugate includes one or more specific-binding molecules (such as antibodies) covalently linked to one or more detectable labels (such as a fluorophore, a luminophore, fluorescent nanoparticles, haptens, enzymes and combinations thereof).

As used herein, the term "couple" or "coupling" refers to the joining, bonding (e.g. covalent bonding), or linking of one molecule or atom to another molecule or atom.

DARPins (designed ankyrin repeat proteins) are genetically engineered antibody mimetic proteins typically exhibiting highly specific and high-affinity target protein binding. They are derived from natural ankyrin proteins and consist of at least three, usually four or five repeat motifs of these proteins.

"Multiplex," "multiplexed," or "multiplexing" refers to detecting multiple targets in a sample concurrently, substantially simultaneously, or sequentially. Embodiments of the present disclosure allow multiple targets in a sample to be detected substantially simultaneously, or sequentially, as desired, using plural different conjugates. Multiplexing can include identifying and/or quantifying peptides, proteins, both individually and in any and all combinations. Multiplexing also can include detecting two or more of a messenger and a protein in a cell in its anatomic context.

The term "primary antibody" refers to an antibody which binds specifically to the target protein antigen in a tissue sample. A primary antibody is generally the first antibody used in an immunohistochemical procedure.

Reactive Groups: Formulas throughout this application refer to "reactive groups," "reactive functional groups," "terminal reactive groups" or the like which can be any of a variety of groups (e.g. functional groups) suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glycols, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbondiimides. Suitable hydroxyl-reactive functional groups include epoxides and oxiranes, carbonyldiimidazole, N,N'-disuccinimidyl carbonates or Nhydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

The term "secondary antibody" herein refers to an antibody which binds specifically to a primary antibody, thereby forming a bridge between the primary antibody and a subsequent reagent (e.g. a label, an enzyme, etc.), if any. The secondary antibody is generally the second antibody used in an immunohistochemical procedure.

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples, with more particular examples including, peripheral blood, urine, saliva, tissue biopsy, surgical specimen, amniocentesis samples and autopsy material.

As used herein the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

Target: Any molecule for which the presence, location and/or concentration is or can be determined. Examples of target molecules include proteins and haptens, such as haptens covalently bonded to proteins. Target molecules are typically detected using one or more conjugates of a specific binding molecule and a detectable label.

Polymers and their Use as Carriers for Labels

The present disclosure is directed to novel polymers, whereby the polymers serve as carriers for labels, such as haptens. One or more of the disclosed polymers may themselves be coupled to specific binding entities, such as antibodies, to form conjugates, such as antibody conjugates, as disclosed herein.

Figure 2:
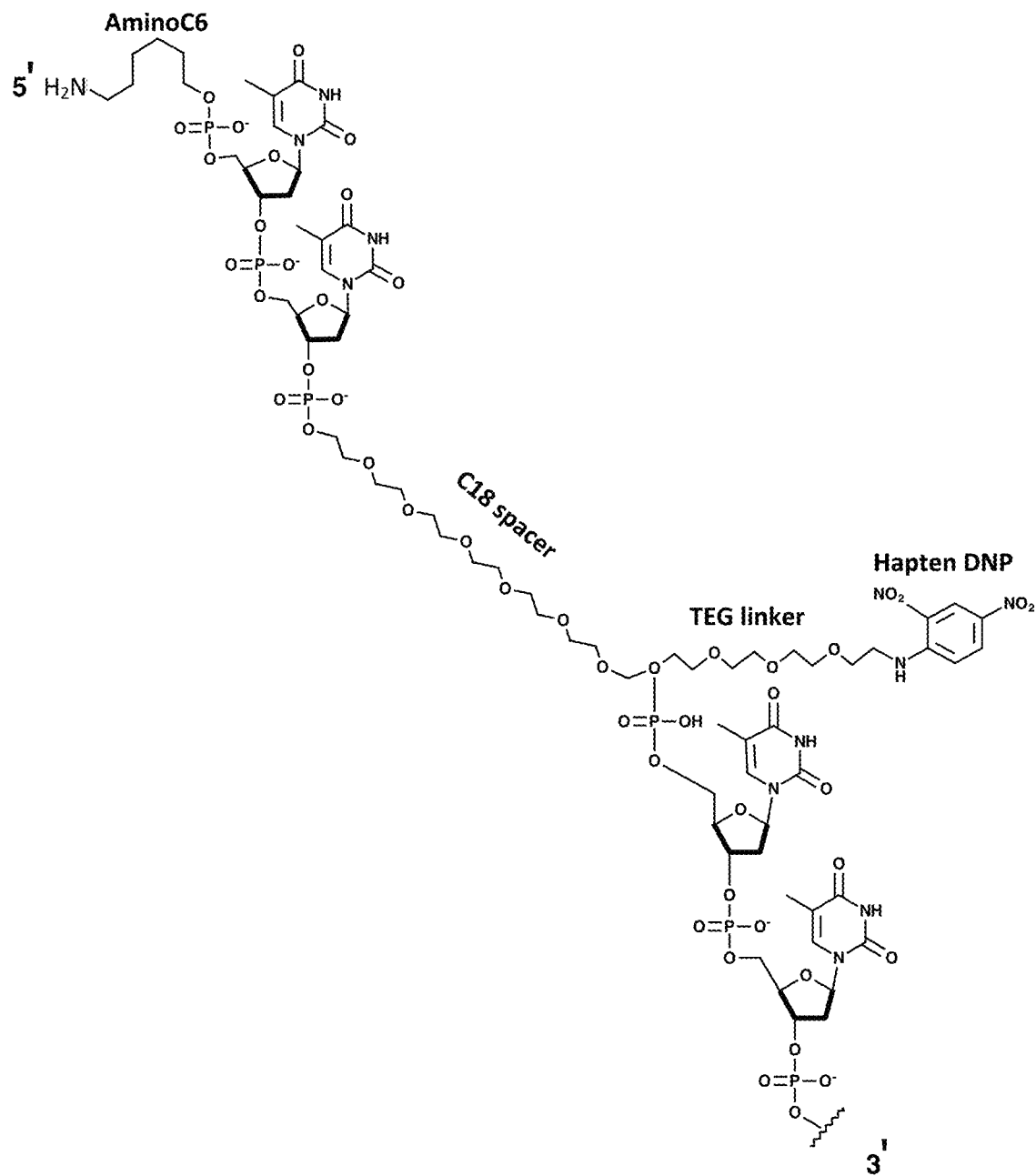
FIG. 2 illustrates an example of an antibody conjugate comprising an oligonucleotide polymer backbone where the backbone further comprises a spacer, and a label attached to the polymer backbone through a linker.
Figure 3:
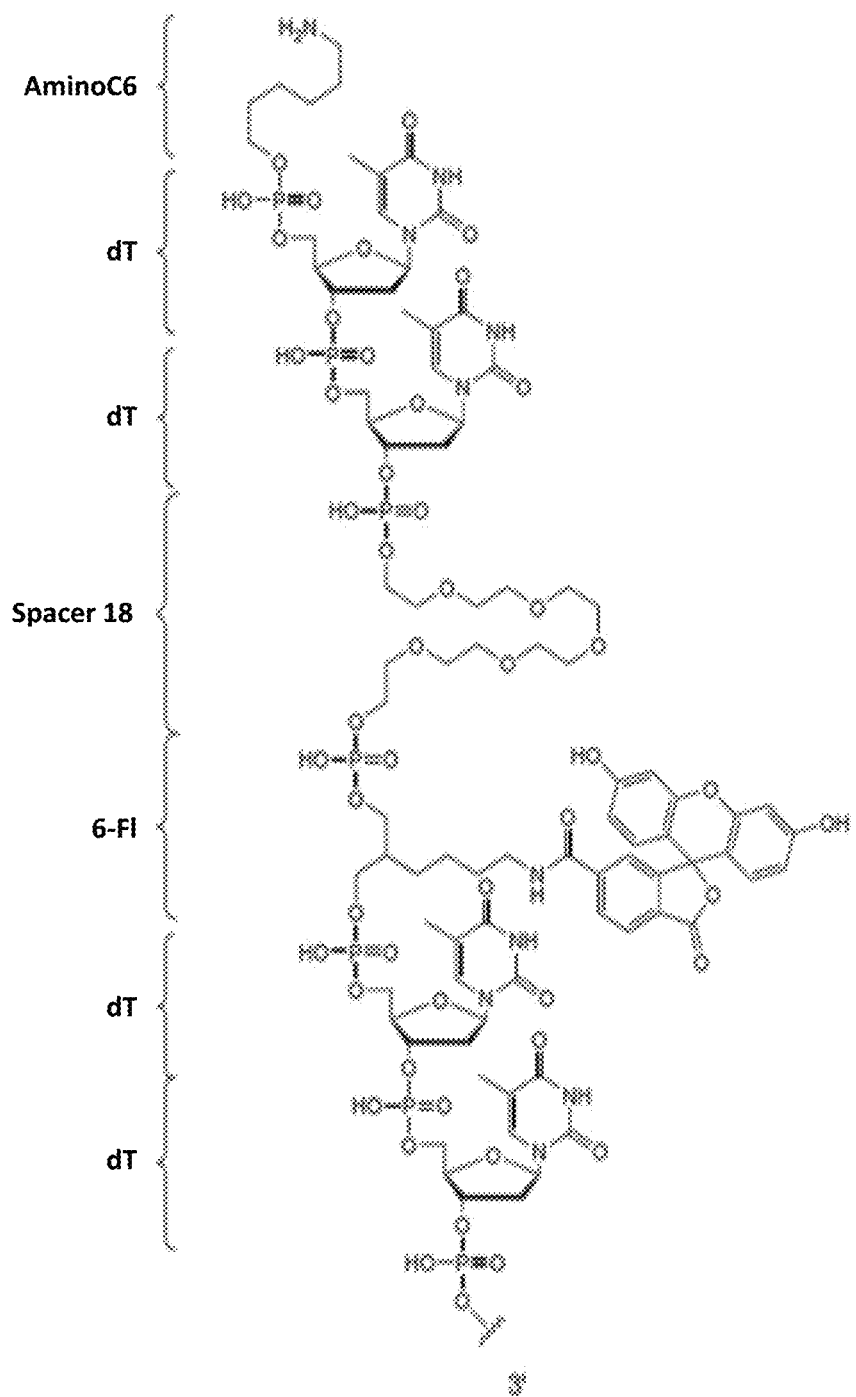
FIG. 3 illustrates an example of an antibody conjugate comprising an oligonucleotide polymer backbone where the backbone further comprises a spacer, and a label attached to the polymer backbone through a linker.

In general, the polymers comprise labels attached directly or indirectly, such as through a linker, to a polymer backbone. For example, the compounds depicted in FIGS. 1, 2, and 3 provide a polymeric backbone comprising oligonucleotides coupled to an optional spacer ("C18 Spacer" of FIG. 2 or "Spacer 18" or FIG. 3), forming a polymeric backbone. Coupled to the polymeric backbone is a label, the label being connected to the backbone through an optional linker ("Hapten DNP" and "TEG Linker" for FIGS. 1 and 2; and "6FI"

for FIG. 3). Thus, as can be seen at least in FIGS. 1, 2, and 3, the polymers serve as a carrier for one or more labels.

The polymers may have the structure of Formula (I):

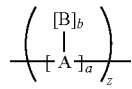

(I)

where A comprises an oligonucleotide sequence and an optional spacer ("polymeric backbone") and B comprises a label and an optional linker; wherein a is an integer ranging from 1 to 8, b is 1 or 2, and z is an integer ranging from 1 to 24. As shown in Formula (I), A and B are repeat groups and the polymer of Formula (I) may terminate on a 5' end with a terminal reactive group (e.g. an amino group, carboxyl group, or sulfhydryl group) and may terminate on a 3' end with a terminal group (non-limiting examples of terminal groups include hydrogen, a hydroxyl group, a carbonyl group, an amino group, a phosphate group, a phosphodiester group, or a cation). Any group [A] or [B], or any of the components or constituents comprising [A] or [B], may be bonded directly to each other or through an optional group as known to those of ordinary skill in the art, e.g. a phosphate group or phosphodiester group. For example, a 'Label' may be bonded to an [Olig] group when no spacer or [Linker] is present, through a group which bridges the [Olig] and 'Label,' and these groups are known to those of skill in the art and include, without limitation, phosphate groups or phosphodiester groups. In some embodiments, a ratio of a:b in Formula (I) is 1:1, 2:1, 1:2, or 3:1. In some embodiments, a size or length of [A] ranges from about 8 nm to about 12 nm. In other embodiments, a size or length of [A] is less than about 8 nm. In other embodiments, a size or length of [A] allows for the labels comprising [B] to be spaced such that they approximate the distance between antigen binding sites of an antibody (e.g. a secondary antibody specific for the label and used to detect the label). In some embodiments, [A] comprises a net neutral charge (e.g. a negatively charges oligonucleotide sequence rendered nearly neutral by a positively charged spacer component).

In some embodiments, a is 1 and b is 1. In other embodiments, a is 2 and b is 1. In some embodiments, z is an integer ranging from 1 to 18. In other embodiments, z is an integer ranging from 2 to 16. In yet other embodiments, z is an integer ranging from 2 to 9. In yet other embodiments, z is an integer ranging from 3 to 9. In yet further embodiments, z is one of 3, 4, 5, or 9.

In some embodiments, [A] has the structure of Formula (II):

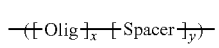

(II)

wherein 'Olig' is an oligonucleotide sequence (e.g. single stranded or double stranded) having between 1 and about 50 nucleotides, wherein the oligonucleotide sequence has a Tm of less than 70° C.; 'Spacer' is a branched or unbranched, substituted or unsubstituted, saturated or unsaturated aliphatic group, optionally having one or more heteroatoms selected from O, N, or S, and having between 4 and 32 carbon atoms; and wherein x is 1 or 2 and y is 0, 1, or 2. In embodiments where y is 0, [Spacer] is a bond, which can couple adjacent [Olig] groups and/or a [B] group ('Label' and/or 'Linker') to the [Olig]. In some embodiments, x is 1 and y is 1. In other embodiments, x is 1 and y is 1. In yet other embodiments, x is 1 and y is 2.

In some embodiments, [B] has the structure of Formula (III):

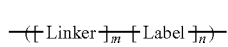

(III)

wherein 'Linker' is a branched or unbranched, substituted or unsubstituted, saturated or unsaturated aliphatic group, optionally having one or more heteroatoms selected from O, N, or S, and having between 4 and 18 carbon atoms 'Label' is selected from the group consisting of haptens, chromogens, enzymes, fluorophores, and quantum dots; and wherein m is 0, 1, or 2, and wherein n is 1 or 2; and when m is 0, then [Linker] is a bond, such that the [Labe] may couple to the polymeric backbone [A]. In some embodiments, m is 1 and n is 1.

In some embodiments, at least one polymer of Formula (I) is coupled to a specific binding entity to form a conjugate, such as provided in Formula (IVa) and (IVb):

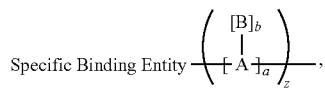

(IVa)

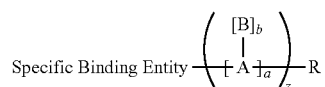

(IVb)

wherein "Specific Binding Entity" represents a specific binding entity, as that term is defined herein (e.g. an antibody, an antibody fragment, a drug/antibody complex, a nucleic acid); R is a terminal group (e.g. hydrogen, a hydroxyl group, a carbonyl group, cation, an amino group, a phosphate group, a phosphodiester group); a and b are integers that each independently range from 1 to 8; and z is an integer that ranges from 1 to 24.

In some embodiments, a plurality of polymers are coupled to the specific binding entity. In other embodiments, between about 1 and about 5 polymers of Formula (I) are coupled to a single specific binding entity (while Formulas (IVa) and (IVb) show only a single bond to the specific binding entity, this is for illustrative purposes only, and the skilled artisan will recognize that multiple polymers may be coupled). In some embodiments, the specific binding entity is an antibody, where the polymers may be coupled to any portion of the antibody (e.g. an Fc portion of the antibody). In some embodiments, between 2 and 5 polymers couple to an antibody, with each polymer comprising between about 3 and about 18 Labels. The skilled artisan will appreciate that a low number of polymers (i.e. a low degree of labeling) prevents or mitigates deleterious effects on antibody activity.

In some embodiments, a is 1 and b is 1. In other embodiments, a is 2 and b is 1. In yet other embodiments, z is an integer ranging from 1 to 18. In other embodiments, z is an integer ranging from 2 to 16. In yet other embodiments, z is an integer ranging from 2 to 9. In yet other embodiments, z is an integer ranging from 3 to 9. In yet further embodiments, z is one of 3, 4, 5, or 9.

In some embodiments, the polymer has the structure of Formula (V):

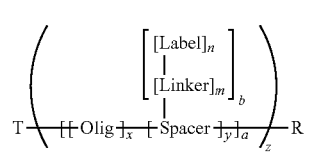

(V)

wherein

'Olig' is a single-stranded oligonucleotide sequence having between 1 and about 50 nucleotides, wherein the oligonucleotide sequence has a Tm of less than 70° C.;

'Spacer' is a branched or unbranched, substituted or unsubstituted, saturated or unsaturated aliphatic group, optionally having one or more heteroatoms selected from O, N, or S, and having between 4 and 32 carbon atoms;

'Linker' is a branched or unbranched, substituted or unsubstituted, saturated or unsaturated aliphatic group, optionally having one or more heteroatoms selected from O, N, or S, and having between 4 and 18 carbon atoms;

'Label' is selected from the group consisting of haptens, fluorophores, chromogens, and enzymes;

R is a terminal group (non-limiting examples include hydrogen, a hydroxyl group, a carbonyl group, an amino group, a phosphate group, a phosphodiester group, or a cation);

T is a group having a terminal reactive moiety;

x is 1 or 2; y is 0, 1, or 2; z is an integer ranging from 1 to 24;

m is 0, 1, or 2; n is 1 or 2;

a is an integer ranging from 1 to 8; b is 1 or 2; and wherein any of the 'Olig', 'Spacer,' or 'Linker' may be bonded directly to each other or through an optional group or reactive group, including, but not limited to, phosphate groups or phosphodiester groups, and wherein when y is 0, [Spacer] is a bond and when m is 0, [Linker] is a bond.

In embodiments where y is zero and [Spacer] is a bond, the [Linker], if present, is coupled or bonded to the [Olig], either directly or through an optional group (e.g. phosphate group or phosphodiester group). In embodiments where m is zero and [Linker] is a bond, the [Label] is coupled or bonded to the [Spacer], either directly or through an optional group (e.g. phosphate group or phosphodiester group). In embodiments where y is zero and m is zero, the [Label] is bonded to the [Olig], either directly or through an optional group (e.g. phosphate group or phosphodiester group).

In some embodiments, a is 1 and b is 1. In other embodiments, a is 2 and b is 1. In some embodiments, z is an integer ranging from 1 to 18. In other embodiments, z is an integer ranging from 2 to 16. In yet other embodiments, z is an integer ranging from 2 to 9. In yet other embodiments, z is an integer ranging from 3 to 9. In yet further embodiments, z is one of 3, 4, 5, or 9.

In some embodiments, x is 1, y is 1, m is 1, n is 1, a is 1 or 2, b is 1, and z is an integer ranging from 1 to 18. In other embodiments, x is 1, y is 0, m is 1, n is 1, a is 1 or 2, b is 1, and z is an integer ranging from 1 to 18. In further embodiments, x is 1, y is 2, m is 1, n is 1, z is 3, 4, 5, or 9, and the Label is fluorescein or a fluorescein derivative. In other embodiments, x is 1, y is 2, m is 1, n is 1, z is 3, 4, 5, or 9, the Label is fluorescein or a fluorescein derivative, and the Spacer comprises between 4 and 12 carbon atoms. In yet further embodiments, x is 1, y is 1, m is 1, n is 1, a is 1 or 2, b is 1, z is an integer ranging from 1 to 18, and the Label is a hapten. In even further embodiments, x is 1, y is 1, m is 1, n is 1, a is 1 or 2, b is 1, z is an integer ranging from 1 to 18, the Label is a hapten, and the Spacer comprises between 4 and 12 carbon atoms. In some embodiments, a ratio of a:b of Formula (V) is 1:1. In other embodiments, a ratio of a:b of Formula (V) is 2:1. In yet other embodiments, a ratio of a:b of Formula (V) is 3:1. In some embodiments, [Olig] comprises an oligonucleotide sequence having between 2 and 24 mer. In some embodiments, [Olig] comprises an oligonucleotide sequence having between 2 and 12 mer.

In some embodiments, T is an aliphatic group comprising between 2 and 8 carbon atoms and a terminal functionality (e.g. a reactive group) that is reactive with appropriate functionality of a specific binding moiety, e.g. an amino group. In some embodiments, T possess the requisite functionality to couple, bond, or otherwise attach to a Specific Binding Entity (e.g. an antibody, a nucleic acid, a drug/antibody complex/conjugate). In other embodiments, T possess the requisite functionality to couple to an amino group, a sulfhydryl group, or a carbohydrate group of an antibody.

In other embodiments, the polymer has the structure of Formula (VIa):

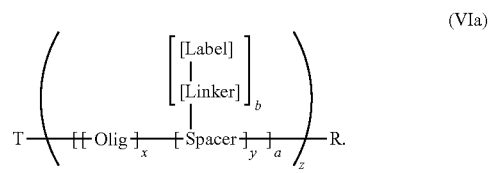

In some embodiments, the polymer of Formula (VIa) comprises a Spacer having between 2 and 12 carbon atoms, a Label selected from one of a hapten or a fluorescein, and where x is 1 and y is 1. In other embodiments, the polymer of Formula (VIa) comprises a Spacer having between 2 and 12 carbon atoms, a Label selected from one of a hapten or a fluorescein, and where x is 1, y is 1, a is 1 or 2, b is 1 or 2, and z is one of 3, 4, 5, or 9. In other embodiments, the polymer of Formula (VIa) comprises a Spacer having between 2 and 12 carbon atoms, a Label selected from one of a hapten or a fluorescein, and where x is 1 and y is 2. In other embodiments, the polymer of Formula (VIa) comprises a Spacer having between 2 and 12 carbon atoms, a Label selected from one of a hapten or a fluorescein, and where x is 1, y is 2, a is 1 or 2, b is 1 or 2, and z is one of 3, 4, 5, or 9. In some embodiments, [Olig] comprises an oligonucleotide sequence having between 2 and 24 mer. In some embodiments, [Olig] comprises an oligonucleotide sequence having between 2 and 12 mer.

In yet other embodiments, the polymer has the structure of Formula (VIb):

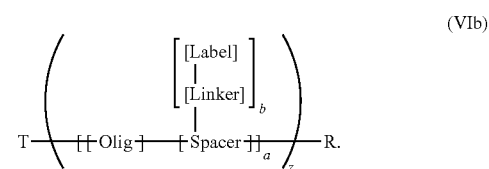

In some embodiments, the polymer of Formula (VIb) comprises a Spacer having between 2 and 12 carbon atoms, a Label selected from one of a hapten or a fluorescein, and where z is one of 3, 4, 5, or 9. In some embodiments, [Olig] comprises an oligonucleotide sequence having between 2 and 24 mer. In some embodiments, [Olig] comprises an oligonucleotide sequence having between 2 and 12 mer.

In yet other embodiments, the polymer has the structure of Formula (VIc):

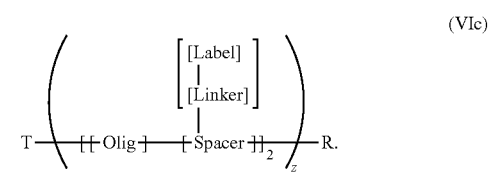

In some embodiments, the polymer of Formula (VIc) comprises a Spacer having between 2 and 12 carbon atoms, a Label selected from one of a hapten or a fluorescein, and where z is one of 3, 4, 5, or 9. In some embodiments, [Olig] comprises an oligonucleotide sequence having between 2 and 24 mer. In some embodiments, [Olig] comprises an oligonucleotide sequence having between 2 and 12 mer.

Of course, the terminal reactive group at the 5' end of any of the polymers of Formulas (V), (VIa), (VIb), and (VIc) may react and couple with the appropriate functionality of a specific binding entity to form the respective conjugate, according to synthetic procedures as known in the art. In some embodiments, the terminal reactive moiety of T is an amino group, a carboxyl group, or a sulfhydryl group. In some embodiments, R is selected from hydrogen, a hydroxyl group, a carbonyl group, an amino group, a phosphate group, a phosphodiester group, or a cation. In some embodiments, R is a cation including those selected from $Na^+$, $K^+$, $Mg^{2+}$, $Mn^{2+}$, $Zn^{2+}$, $NH_4^+$, $H_3O^+$. In some embodiments R is a carboxylic acid. By way of example only, R may be $O^-R$, where R is a cation.

In some embodiments, at least one polymer of Formula (I), Formula (V), or Formula (VIa to VIc), or any combination thereof, are coupled to a specific binding entity to form a conjugate, such as depicted in Formula (VId):

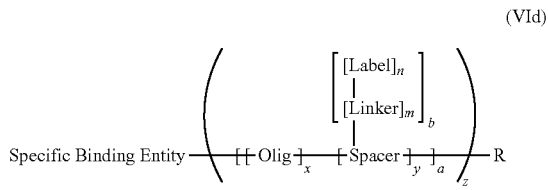

(VId)

wherein 'Olig' is a single or double stranded oligonucleotide sequence having between 1 and about 32 nucleotides, the oligonucleotide sequence has a Tm of less than 70° C.; 'Spacer' is a branched or unbranched, substituted or unsubstituted, saturated or unsaturated aliphatic group, optionally having one or more heteroatoms selected from O, N, or S, and having between 4 and 24 carbon atoms; 'Linker' is an aliphatic group, optionally having one or more heteroatoms selected from O, N, or S, and having between 4 and 18 carbon atoms; 'Label' is selected from the group consisting of haptens, enzymes, chromogens, fluorophores, and quantum dots; 'Specific Binding Entity' is an antibody, antibody fragment, nucleic acid, or drug/antibody conjugate; R is a terminal group (non-limiting examples include hydrogen, a hydroxyl group, an amino group, a carbonyl group, a phosphate group, a phosphodiester group, or a cation); x is 1 or 2; y is 0, 1, or 2; z is an integer ranging from 1 to 18; a is an integer ranging from 1 to 8; b is an integer ranging from 1 to 8; wherein any of the 'Olig,' Spacer,' or 'Linker' may be bonded directly to each other or through an optional group, and wherein when y is 0 the [Spacer] is a bond, and when m is 0 the [Linker] is a bond. In embodiments where y is zero and [Spacer] is a bond, the [Linker], if present, is coupled or bonded to the [Olig], either directly or through an optional group (e.g. phosphate group or phosphodiester group). In embodiments where m is zero and [Linker] is a bond, the [Label] is coupled or bonded to the [Spacer], either directly or through an optional group (e.g. phosphate group or phosphodiester group). In embodiments where y is zero and m is zero, the [Label] is bonded to the [Olig], either directly or through an optional group (e.g. phosphate group or phosphodiester group).

In some embodiments, x is 1, y is 1, m is 1, n is 1, a is 1 or 2, b is 1, and z is an integer ranging from 1 to 18. In other embodiments, x is 1, y is 0, m is 1, n is 1, a is 1 or 2, b is 1, and z is an integer ranging from 1 to 18 (where [Spacer] is a bond and where the [Linker] is coupled to the [Olig]). In further embodiments, x is 1, y is 2, m is 1, n is 1, z is 3, 4, 5, or 9, and the Label is fluorescein or a fluorescein derivative. In other embodiments, x is 1, y is 2, m is 1, n is 1, z is 3, 4, 5, or 9, the Label is fluorescein or a fluorescein derivative, and the Spacer comprises between 4 and 12 carbon atoms. In yet further embodiments, x is 1, y is 1, m is 1, n is 1, a is 1 or 2, b is 1, z is an integer ranging from 1 to 18, and the Label is a hapten. In even further embodiments, x is 1, y is 1, m is 1, n is 1, a is 1 or 2, b is 1, z is an integer ranging from 1 to 18, the Label is a hapten, and the Spacer comprises between 4 and 12 carbon atoms. In some embodiments, a ratio of a:b of Formula (V) is 1:1. In other embodiments, a ratio of a:b of Formula (V) is 2:1. In yet other embodiments, a ratio of a:b of Formula (V) is 3:1. In some embodiments, [Olig] comprises an oligonucleotide sequence having between 2 and 24 mer. In some embodiments, [Olig] comprises an oligonucleotide sequence having between 2 and 12 mer.

In some embodiments, a plurality of polymers are coupled to the specific binding entity. In other embodiments, between about 1 and about 5 polymers of Formulas V, VIa, VIb, VIc, or VId (or any combination thereof) are coupled to a single specific binding entity. In some embodiments, the conjugates of Formula (VId) are used as detection probes which, by means of the Specific Binding Entity provided, associate with a target in a tissue sample (e.g. to form a conjugate-target complex). The skilled artisan will, of course, recognize that multiple different conjugates of Formula (VId) may be used in conjugate with each other to facilitate the detection of multiple targets (e.g. multiple gene expression products and/or multiple target nucleic acid sequences).

Oligonucleotides

The polymers of the present disclosure utilize oligonucleotides as constituent parts of a polymeric backbone which, as described herein, which allows the polymer to serve as a carrier for one or more labels. In some embodiments, the oligonucleotide sequences comprise between about 1 and about 50 nucleotides ("mers") or between about 2 and about 50mers (i.e. [Olig] of $[Olig]_x$ comprises between 1 and 50mer, and where x is greater than one, the group $[Olig]_x$ may contain more than 50mer). In some embodiments, the oligonucleotide sequences have a melting temperature ($T_m$) of less than about 70° C. In other embodiments, the oligonucleotide sequences have a melting temperature ($T_m$) of less than about 37° C. In other embodiments, the oligonucleotide sequence comprises less than 35mers. In yet other embodiments, the oligonucleotide sequence comprises between 2 and 24 mer. In yet further embodiments, the oligonucleotide sequence comprises 20 mer or less. In some embodiments, the oligonucleotide is a hexamer. In some embodiments, the sequences are selected such that they do not form self-complimentary structures.

In general, the oligonucleotide sequence may have any sequence, without limitation. In some embodiments, the oligonucleotide sequence is homogenous, i.e. comprising a single nucleotide (e.g. a poly-T sequence). In other embodiments, the oligonucleotide sequence is heterogeneous, i.e. comprising multiple nucleotides, and the nucleotides may be organized randomly or within repeat groups. In yet other embodiments, the sequence can be designed to encode particular information, such as a bar code, as opposed to functioning solely as a carrier. Specific exemplary disclosed embodiments concern using TATTTT as a building block oligonucleotide, with particular disclosed oligonucleotide embodiments including:

```
24-mer:
TATTTT TATTTT TATTTT TATTTT
(T_m 36.9° C.)(SEQ ID NO: 1)

30-mer:
TATTTT TATTTT TATTTT TATTTT TATTTT
(T_m 42.5° C.) (SEQ ID NO: 2)

42-mer:
TATTTT TATTTT TATTTT TATTTT TATTTT TATTTT TATTTT
(T_m 48.9° C.) (SEQ ID NO: 3)

54-mer:
TATTTT TATTTT TATTTT TATTTT TATTTT TATTTT TATTTT
TATTTT TATTTT
(T_m 52.4° C.) (SEQ ID NO: 4)
```

In some embodiments, the oligonucleotide sequences are single stranded. In other embodiments, the oligonucleotide sequences are double stranded. In yet other embodiments, the oligonucleotide sequences may be chemically modified. In yet further embodiments, the oligonucleotide is antisense to a sequence of interest.

The nucleotides constituting the oligonucleotide may be naturally occurring or synthetic. Suitable oligonucleotides may be composed of naturally occurring nucleosides adenosine, guanosine, cytidine, thymidine and uridine, modified nucleosides, substituted nucleosides or unsubstituted nucleosides, purine or pyrimidine base, or combinations thereof. Such purine and pyrimidine bases include, but are not limited to, natural purines and pyrimidines such as adenine, cytosine, thymine, guanine, uracil, or other purines and pyrimidines, such as isocytosine, 6-methyluracil, 4,6-di-hydroxypyrimidine, hypoxanthine, xanthine, 2,6-diaminopurine, 5-azacytosine, 5-methyl cystosine, and the like. The nucleosides may also be unnatural nucleosides. The nucleosides may be joined by naturally occurring phosphodiester linkages or modified linkages. The nucleosides may also be joined by phosphorothioate linkages or methylphosphonate linkages.

Labels

The labels coupled to the polymeric backbone (see, e.g., Formula (I)) may be selected from haptens, fluorophores, chromogens, enzymes, ligands, phosphorescent or chemiluminescent agents, or quantum dots or any other suitable entity. The type of label selected depends on the polymer being synthesized and the polymer's ultimate role after conjugation to an appropriate specific binding entity. For example, in some embodiments labels may be chosen such that when the polymers are conjugated to an antibody, the labels may be directly detected (e.g. fluoresceins or fluorescein derivatives or analogs). In other embodiments, labels may be selected such that when the polymers are conjugated to an antibody, the labels may be indirectly detected (e.g. detection of a hapten label by using a secondary antibody specific for the hapten, where the secondary antibody is conjugated to a detectable moiety). Guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987), the disclosures of which are incorporated herein by reference.

"Haptens" are small molecules that can combine specifically with an antibody, but typically are substantially incapable of being immunogenic except in combination with a carrier molecule. In some embodiments embodiments, haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans. Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety. The haptens themselves may be suitable for direct detection, i.e. they may give off a suitable signal for detection.

Fluorophores belong to several common chemical classes including coumarins, fluoresceins (or fluorescein derivatives and analogs), rhodamines, resorufins, luminophores and cyanines. Additional examples of fluorescent molecules can be found in The Handbook—A Guide to Fluorescent Probes and Labeling Technologies, Molecular Probes, Eugene, Oreg.

Where the label includes an enzyme a detectable substrate (i.e. a substrate of the enzyme) such as a chromogenic moiety, a fluorogenic compound, or a luminogenic compound can be used in combination with the enzyme to generate a detectable signal (a wide variety of such compounds are commercially available, for example, from Invitrogen Corporation, Eugene Oreg.). Particular examples of chromogenic compounds/substrates include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein).

In some embodiments, the 'Label' is selected from the group consisting of di-nitrophenyl, biotin, digoxigenin, fluorescein, rhodamine, or combinations thereof. In other embodiments, the 'Label' is selected from the group consisting of oxazoles, pyrazoles, thiazoles, nitroaryls, benzofurans, triterpenes, ureas, thioureas, rotenoids, coumarins, cyclolignans, or combinations thereof. In yet other embodiments, the 'Label' is selected from the group consisting of 5-nitro-3-pyrazole carbamide, 2-(3,4-dimethoxyphenyl)quinoline-4-carboxylic acid), 3-hydroxy-2-quinoxalinecarbamide, 2,1,3-benzoxadiazole-5-carbamide, and 2-acetamido-4-methyl-5-thiazolesulfonamide.

The skilled artisan will be able to select an appropriate number of labels for incorporation into the polymer, and the number of labels may vary based on whether detection will be direct or indirect. In some embodiments, the number of labels ranges from 1 to 36 labels per polymer. In other embodiments, the number of labels ranges from 3 to 24 labels per polymer having Formula (I). In yet other embodiments, the number of labels ranges from 3 to 18 labels per polymer having Formula (I). In yet further embodiments, the number of labels ranges from 3 to 12 labels per polymer having Formula (I). In other embodiments, the number of labels is selected from 3 labels, 5, labels, 9 labels, 12 labels, and 18 labels per polymer having Formula (I). Of course, as multiple polymers are coupled to a single specific binding moiety, the number of labels per specific binding moiety increases as a function of the number of polymers and the number of labels conjugated thereto. For example, in reference to an antibody having four coupled polymers, with each polymer having 9 labels, this prophetic antibody conjugate will have 36 labels which may be directly detected or indirectly detected.

Spacers

The polymers optionally comprise one or more Spacers. In some embodiments, a 'Spacer' is a branched or unbranched, substituted or unsubstituted, saturated or unsaturated group (e.g. aliphatic group), optionally having one or more heteroatoms selected from O, N, or S, and having between 4 and 32 carbon atoms. In other embodiments, a 'Spacer' is a branched or unbranched, substituted or unsubstituted, saturated or unsaturated group (e.g. aliphatic group), optionally having one or more heteroatoms selected from O, N, or S, and having between 4 and 24 carbon atoms. In yet other embodiments, a 'Spacer' is a linear chain, which may be substituted or unsubstituted, and may optionally have one or more hetero atoms selected from O, N, or S, and having between 4 and 24 carbon atoms.

In some embodiments, the entire 'Spacer' constitutes part of the polymeric backbone. For example, assuming a 'Spacer' having a structure of that of Formula (IX) herein, both ends of the 'Spacer' are coupled to [Olig] groups and other functionality of the 'Spacer' couples a [B] group ([Label] and/or [Linker]) to the [Spacer]. In some embodiments where the entire 'Spacer' constitutes part of the polymeric backbone, the [B] group ([Label] and/or [Linker]) is coupled to a terminal or 3' portion of the 'Spacer.'

In other embodiments, such as where the 'Spacer' is branched or where the 'Spacer' is substituted, some constituent parts of the 'Spacer' may form part of the backbone [A], while other constituent parts form side-chains or assist with the coupling of a [B] group to the 'Spacer.' In other embodiments, at least four carbon atoms or a combination of four carbon atoms and heteroatoms of any 'Spacer' comprise part of the polymeric backbone (see, e.g. [A] of Formula (I)).

In other embodiments, at least six carbon atoms or a combination of six carbon atoms and heteroatoms of any 'Spacer' comprise part of the polymeric backbone.

In some embodiments, the 'Spacer' has the structure depicted in Formula (VII):

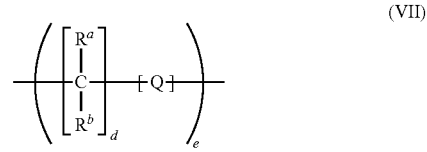

wherein d and e are integers each independently ranging from 1 to 32; Q is a bond, O, S, $N(R^c)(R^d)$ or a quaternary amine $(N^+H(R^c)(R^d))$; $R^a$ and $R^b$ are independently H, a $C_1$-$C_4$ alkyl group, F, Cl, or $N(R^c)(R^d)$; and $R^c$ and $R^d$ are independently $CH_3$ or H. In some embodiments, d and e are integers each independently ranging from 2 to 18. In some embodiments, d is an integer ranging from 1 to 8, and e is an integer ranging from 2 to 16. In other embodiments, d is an integer ranging from 2 to 8, and e is an integer ranging from 2 to 12. In some embodiments, the entire 'Spacer' of Forma (VII) is incorporated within the polymeric backbone [A].

In other embodiments, the 'Spacer' has the structure depicted in Formula (VIII):

wherein d and e are integers each independently ranging from 1 to 32; Q is a bond, O, S, or $N(R^c)(R^d)$; and $R^c$ and $R^d$ are independently $CH_3$ or H. In other embodiments, Q is O. In some embodiments, d is an integer ranging from 1 to 8, and e is an integer ranging from 2 to 16. In other embodiments, d is an integer ranging from 2 to 8, and e is an integer ranging from 2 to 12. In some embodiments, the entire 'Spacer' of Forma (VIII) is incorporated within the polymeric backbone [A].

In yet other embodiments, the 'Spacer' has the structure depicted in Formula (IX):

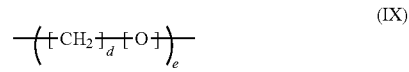

wherein d and e are integers each independently ranging from 1 to 32. In some embodiments, d ranges from 1 to 4, and e ranges from 1 to 8. In some embodiments, d is an integer ranging from 1 to 8, and e is an integer ranging from 2 to 16. In other embodiments, d is an integer ranging from 2 to 8, and e is an integer ranging from 2 to 12. In some embodiments, the entire 'Spacer' of Forma (IX) is incorporated within the polymeric backbone [A].

Additional heterobifunctional polyalkyleneglycol spacers useful for practicing certain disclosed embodiments of the present disclosure are described in assignee's co-pending applications, including "Nanoparticle Conjugates," U.S. patent application Ser. No. 11/413,778, filed Apr. 28, 2006; "Antibody Conjugates," U.S. application Ser. No. 11/413, 415, filed Apr. 27, 2006; and "Molecular Conjugate," U.S.

Provisional Patent Application No. 60/739,794, filed Nov. 23, 2005; all of which applications are incorporated herein by reference.

In some embodiments, the constituent components of the 'Spacer' are selected such that the 'Spacer' has a net positive charge. Without wishing to be bound by any particular theory, it is believed that a 'Spacer' having a net positive charge could balance out any net negative charge typically associated with oligonucleotide sequences of the polymer. Thus, it is believed that the charge of the [Spacer] or of [Olig]-[Spacer] may be modified such that the polymeric backbone may provide a specific electronic configuration.

In some embodiments, suitable spacers are of sufficient length and/or size such that any steric hindrance between the polymer backbone components, including the Labels, may be minimized. Likewise, particular functional groups may be selected to minimize steric interactions or other chemical and/or physical interactions. In some embodiments, the spacer may be chosen, for example, to minimize steric hindrance between consecutive oligonucleotide components or Label components.

In some embodiments, the 'Spacer' and 'Olig' components, as well as the number of times each of these components are repeated per repeat group, are selected such that a size or length of $-([Oligo]_x-[Spacer]_y)_a-$ is optimized. By "optimized," it is meant that the "Olig" and "Spacer" components (or constituent parts of these groups) and/or number of times each are repeated, are selected such that the structure of the polymeric backbone enables the labels attached thereto to be arranged so that they are spaced or are arranged in space (e.g. to have a certain spatial conformation or electronic configuration) to approximate the distance between antigen binding sites of an antibody (e.g. a secondary anti-label antibody). For example, and with reference to Formula (I), in some embodiments, the constituent components of [A] and the number of times [A] is repeated relative to [B] are optimized such that Labels attached to the polymer backbone are spaced a distance apart from each other that approximates the distance between antigen binding sites of a secondary antibody, where the secondary antibody is an anti-Label antibody used for detection for the labels. Of course the skilled artisan will recognize that although a size or length of $-([Oligo]_x-[Spacer]_y)_a-$ may be larger or smaller than the distance between antigen binding sites, there is "flexibility" within the polymeric backbone which allows it to conform in space and "adapt" to the distance between antigen binding sites.

Figure 4:
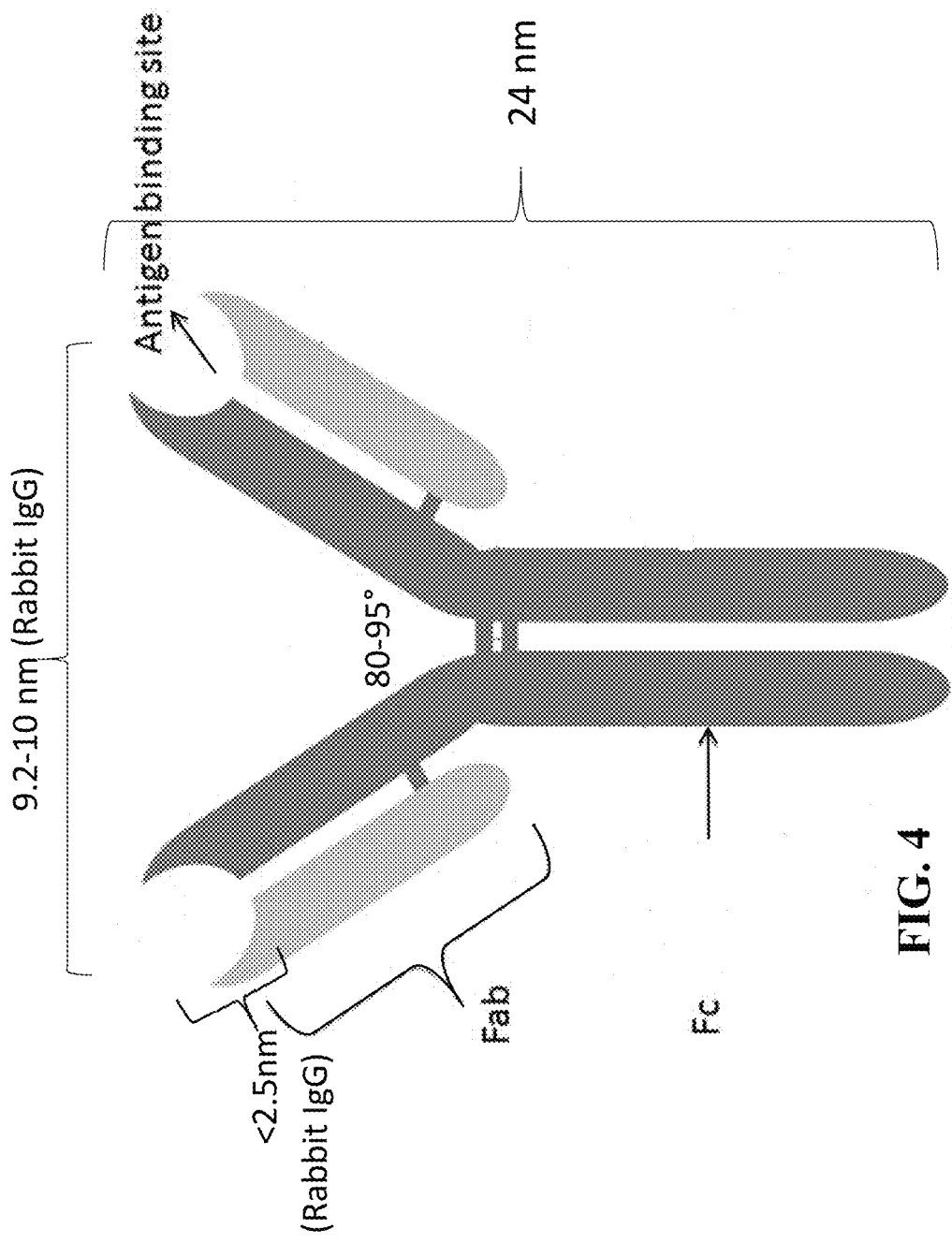
FIG. 4 illustrates an antibody and shows the distance between antigen binding sites.

For example, in some embodiments, the constituent parts of $-([Oligo]_x-[Spacer]_y)_a-$ are selected such that a length of $-([Oligo]_x-[Spacer]_y)_a-$ is about the same as the distance between antigen binding sites of an antibody (see FIG. 4). In other embodiments, the constituent parts of $-([Oligo]_x-[Spacer]_y)_a-$ are selected such that a length of $-([Oligo]_x-[Spacer]_y)_a-$ is less than the distance between antigen binding sites of an antibody. In other embodiments, the constituent parts of $-([Oligo]_x-[Spacer]_y)_a-$ are selected such that a length of $-([Oligo]_x-[Spacer]_y)_a-$ is less than about 12 nm. In other embodiments, the constituent parts of $-([Oligo]_x-[Spacer]_y)_a-$ are selected such that a length of $-([Oligo]_x-[Spacer]_y)_a-$ is less than about 10 nm. In other embodiments, the constituent parts of $-([Oligo]_x-[Spacer]_y)_a-$ are selected such that a length of $-([Oligo]_x-[Spacer]_y)_a-$ is less than about 9.5 nm. In other embodiments, the constituent parts of $-([Oligo]_x-[Spacer]_y)_a-$ are selected such that a length of $-([Oligo]_x-[Spacer]_y)_a-$ is between about 8 nm and about 12 nm. In yet other embodiments, the constituent parts of $-([Oligo]_x-[Spacer]_y)_a-$ are selected such that a length of $-([Oligo]_x-[Spacer]_y)_a-$ is between 1 nm and about 3 nm. Of course, the skilled artisan will recognize that the constituent parts of $-([Oligo]_x-[Spacer]_y)_a-$ selected and the resulting length are based on the particular antibody being utilized. It is believed that by introducing such distances into $-([Oligo]_x-[Spacer]_y)_a-$, it is possible to optimally position and space labels for maximum detection sensitivity and/or binding of the labels by other specific binding entities (e.g. secondary antibodies) (see FIG. 4).

Linkers

The polymers optionally comprise one or more Linkers. In some embodiments, a 'Linker' is a branched or unbranched, substituted or unsubstituted, saturated or unsaturated group (e.g. aliphatic group), optionally having one or more heteroatoms selected from O, N, or S, and having between 4 and 18 carbon atoms.

In some embodiments, the entire 'Linker' bridges and couples the polymeric backbone [A] to the 'Label.' For example, assuming a 'Linker' having a structure of that of Formula (IX) herein, one end of the 'Linker' is coupled to the polymeric backbone [A] while the other end is coupled to the 'Label,' and the 'Linker' may be coupled to either the polymeric backbone [A] or the 'Label' directly or through an optional group including, but not limited to, a phosphate group or a phosphodiester group. In some embodiments, at least four carbon atoms or a combination of four carbon atoms and heteroatoms of any 'Linker' comprises part of the 'bridge' coupling the polymeric backbone to the 'Label.'

In some embodiments, the 'Linker' has the structure depicted in Formula (VII):

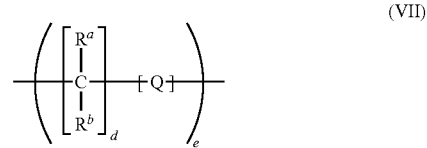

(VII)

wherein d and e are integers each independently ranging from 4 to 18; Q is a bond, O, S, or $N(R^c)(R^d)$; $R^a$ and $R^b$ are independently H, a $C_1$-$C_4$ alkyl group, F, Cl, or $N(R^c)(R^d)$; and $R^c$ and $R^d$ are independently $CH_3$ or H. In some embodiments, d and e are integers each independently ranging from 4 to 12.

In other embodiments, the 'Linker' has the structure depicted in Formula (VIII):

(VIII)

wherein d and e are integers each independently ranging from 4 to 18; Q is a bond, O, S, or $N(R^c)(R^d)$; and $R^c$ and $R^d$ are independently $CH_3$ or H. In other embodiments, Q is O.

In yet other embodiments, the 'Linker' has the structure depicted in Formula (IX):

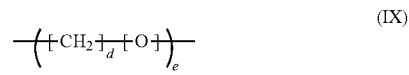

(IX)

wherein d and e are integers each independently ranging from 4 to 18. In some embodiments, d ranges from 4 to 8.

The alkylene oxides 'Linkers' are represented herein by reference to glycols, such as ethylene glycols. Hapten conjugates of the present disclosure have proved particularly useful if the hydrophilicity of the 'Linker' is increased relative to their hydrocarbon chains. As a result, the alkylene oxides, such as the glycols, have proved useful for practicing this disclosure. A person of ordinary skill in the art will appreciate that, as the number of oxygen atoms increases, the hydrophilicity of the compound also may increase. Thus, 'Linkers' of the present disclosure generally have the structure as depicted by Formula (VII), (VIII), and (IX), where Q is oxygen. Additional heterobifunctional polyalkyleneglycol spacers useful for practicing certain disclosed embodiments of the present disclosure are described in assignee's co-pending applications, including "Nanoparticle Conjugates," U.S. patent application Ser. No. 11/413,778, filed Apr. 28, 2006; "Antibody Conjugates," U.S. application Ser. No. 11/413,415, filed Apr. 27, 2006; and "Molecular Conjugate," U.S. Provisional Patent Application No. 60/739,794, filed Nov. 23, 2005; all of which applications are incorporated herein by reference.

Examples of Polymers

Polymer Example 1

In one particular embodiment, the polymer has the structure provided in Formula (Xa):

5' (AminoC6)-TATTTT[DNP]TATTTT[DNP]TATTTT
[DNP]T (Xa) (SEQ ID NO: 5), where AminoC6 represents a terminal functional group (e.g. reactive group) having six carbon atoms and a primary or secondary amine that may couple to a specific binding entity; [TATTTT] is a oligonucleotide sequence; and DNP is a hapten. In this particular example, no 'Spacer' is present, and the DNP is coupled to the polymeric backbone through a 'Linker' (not depicted). While the oligonucleotide sequence is depicted in this example as [TATTT], longer or shorter sequences having any combination of nucleotides may be utilized. This particular embodiment is depicted as comprising three labels and three oligonucleotide sequences. Of course, this particular embodiment may be modified to include spacers.

Polymer Example 2

5' (AminoC6)-TATTTT[DNP]TATTTT[DNP]TATTTT
[DNP]TATTTT[DNP]T (Xb) (SEQ ID NO: 6)

Example 2 is similar to the polymer of Example 1 except that it contains four labels and four oligonucleotide sequences. Like Example 1, this particular embodiment may be modified to include spacers and the DNP may be coupled to the backbone via a linker.

Polymer Example 3

In another particular embodiment, the polymer has the structure provided in Formula (Xc):

5' (AminoC6)-TATTTT[DNP]TATTTT[DNP]TATTTT
[DNP]TATTTT[DNP]TATTTT[DNP]T (Xc) (SEQ ID NO: 7), where AminoC6 represents a terminal functional group that may couple to a specific binding entity; [TATTTT] is a oligonucleotide sequence; and DNP is a hapten. In this particular example, no 'Spacer' is present, and DNP is coupled to the polymeric backbone through a 'Linker' (not depicted). While the oligonucleotide sequence is depicted in this example as [TATTT], longer or shorter sequences having any combination of nucleotides may be utilized. While this particular embodiment is depicted as comprising five labels and five oligonucleotide sequences, also contemplated is a variant comprising nine labels and nine oligonucleotide sequences, as provided in Example 4 below. Examples 3 and 4 may be modified to include spacers.

Polymer Example 4

Example 4 is similar to the polymer of Example 3 except that it contains nine labels and nine oligonucleotide sequences. Like Example 3, this particular embodiment may be modified to include spacers and the DNP may be coupled to the backbone via a linker.

5' (AminoC6)-TATTTT[DNP]TATTTT[DNP]TATTTT

[DNP]TATTTT[DNP]TATTTT[DNP]TATTTT[DNP]TA

TTTT[DNP]TATTTT[DNP]TATTTT[DNP]T (Xd) (SEQ ID NO: 8),

Polymer Example 5

In another particular embodiment, the polymer has the structure provided in Formula (Xe):

5' (AminoC6)-TA[Sp~C18][DNP]TA[Sp~C18][DNP]

TA[Sp~C18][DNP]TA[Sp~C18][DNP]TA[Sp~C18]

[DNP]TA[Sp~C18][DNP]TA[Sp~C18][DNP]TA[Sp~C18]

(Xe), where AminoC6 represents a terminal functional group that may conjugate to a specific binding entity; [TA] is an oligonucleotide sequence; [SP~C18] is a spacer comprising at least 18 atoms, and DNP is a hapten. DNP is coupled to the polymeric backbone through a 'Linker' (not depicted). While the oligonucleotide sequence is depicted in this example as [TA], longer sequences having any combination of nucleotides may be utilized. While this particular embodiment comprises nine labels, nine spacers, and nine oligonucleotide sequences, also contemplated are similar variants comprising five labels, five spacers, and five oligonucleotide sequences; and those similar variants comprising three labels, three spacers, and three oligonucleotide sequences.

Polymer Example 6

In another particular embodiment, the polymer has the structure provided by Formula (Xf):

5' (AminoC6)-TA[Sp~C18][Fl]TA[Sp~C18][Fl]TA

[Sp~C18][Fl]TA[Sp~C18][Fl]TA[Sp~C18][Fl]TA

[Sp~C18][Fl]TA[Sp~C18][Fl]TA[Sp~C18][Fl]TA

[Sp~C18][Fl]T (Xf), where AminoC6 represents a terminal functional group that may couple to a specific binding entity; [TA] is a oligonucleotide sequence; [SP~C18] is a spacer comprising at least 18 atoms; and [Fl] is a fluorophore, such as fluorescein (or a fluorescein derivative). Fl is coupled to the polymeric backbone through a 'Linker' (not depicted). While the oligonucleotide sequence is depicted in this example as [TA], longer sequences having any combination of nucleotides may be utilized. While this particular embodiment comprises nine labels, nine spacers, and nine oligonucleotide sequences, also contemplated are similar variants comprising five labels, five spacers, and five oligonucleotide sequences; those similar variants comprising four labels, four spacers, and four oligonucleotide sequences; and those similar variants comprising three labels, three spacers, and three oligonucleotide sequences.

Polymer Example 7

In another particular embodiment, the polymer has the structure provided by Formula (Xg):

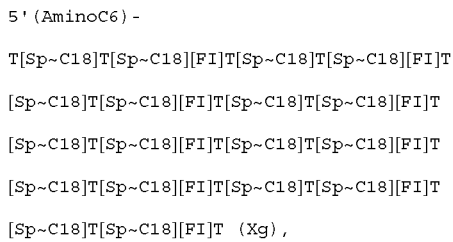

```
5'(AminoC6)-

T[Sp~C18]T[Sp~C18][Fl]T[Sp~C18]T[Sp~C18][Fl]T

[Sp~C18]T[Sp~C18][Fl]T[Sp~C18]T[Sp~C18][Fl]T

[Sp~C18]T[Sp~C18][Fl]T[Sp~C18]T[Sp~C18][Fl]T

[Sp~C18]T[Sp~C18][Fl]T[Sp~C18]T[Sp~C18][Fl]T

[Sp~C18]T[Sp~C18][Fl]T   (Xg),
``` where AminoC6 represents a terminal functional group that may couple to a specific binding entity; [T] is a oligonucleotide sequence; [SP⁻C18] is a spacer comprising at least 18 atoms; and [Fl] is a fluorophore, such as fluorescein (or a fluorescein derivative). Fl is coupled to the polymeric backbone through a 'Linker' (not depicted). In this particular embodiment, the polymeric backbone comprises two oligonucleotide sequences and two spacers, in alternating arrangement. The [Fl] group is conjugated to this polymeric backbone. While the oligonucleotide sequence is depicted in this example as [T], longer sequences having any combination of nucleotides may be utilized. While this particular embodiment comprises nine labels, nine spacers, and nine oligonucleotide sequences, also contemplated are similar variants comprising five labels, five spacers, and five oligonucleotide sequences; those similar variants comprising four labels, four spacers, and four oligonucleotide sequences; and those similar variants comprising three labels, three spacers, and three oligonucleotide sequences.

Polymer Conjugates

In some embodiments, the polymers described herein may be coupled to a specific binding entity such as provided in Formulas (IVa), (IVb), or (VId). In some embodiments, at least one polymer is coupled to a specific binding entity. In other embodiments, a plurality of polymers, including those of any of Formulas (I), (V), (VIa), (VIb), or (VIc) or in Formulas (Xa through Xg) are coupled to a specific binding entity. In some embodiments, the specific binding entity is a nucleic acid sequence. In other embodiments, the specific binding entity is an antibody, e.g. a primary antibody. In yet other embodiments, the specific binding entity is an drug/antibody conjugate.

It is believed that the conjugates disclosed herein may serve as detection probes and may be utilized in ISH, IHC, and other assays (e.g. immuno-detection assays, flow cytometry, microscopy, imagining, high contrast content screening, immunocytochemistry assays, immunomagnetic cellular depletion assays, immunomagnetic cell capture assays, enzyme immune-assay, enzyme linked immune-assay, etc.).

In some embodiments, the polymer conjugates are suitable for use in multiplex detection assays. In some embodiments, the conjugates described herein serve as detection probes such that targets within a tissue sample may be detected. For example, polymer-antibody conjugates may be used to detect certain gene expression products. For example, the polymer-antibody conjugate may comprise an antibody that detects a protein associated with cancer, such as a HER2/neu (or HER2 protein), c-Myc, n-Myc, Abl, EGFR protein, TOP2A, Bcl2, Bcl6, $R^b1$, p53, or c-Met primary antibody. Other targets which may be detected with the conjugates of the present disclosure (including antibody conjugates ad nucleic acid conjugates) are further described herein (but by no means limited to those examples provided herein).

In some embodiments, one or more polymers are coupled to a primary antibody to form a polymer-antibody-conjugate ("conjugate" or "antibody conjugate"). The number of polymers which may be coupled to any particular primary antibody depends, of course, on the particular antibody selected and its physical and/or chemical properties. In some embodiments, a degree of labeling of the number of polymers per antibody ranges from between about 2 and about 4, as determined by the absorption spectra of such conjugated antibodies. In other embodiments, the degree of labeling is greater than about 2. In other embodiments, the degree of labeling is about 2.5, or 2.3, or 2.1. In yet other embodiments, the degree of labeling is about 4. Without wishing to be bound by any particular theory, it is believed that a relatively low degree of labeling prevents or mitigates any deleterious effects on antibody functionality (e.g. antigen binding or long-term stability of the labeled antibody). For example, a low number of polymers (having the configurations noted herein) attached to the specific binding entity is believed to prevent prevent or mitigate steric interactions.

The polymers may be coupled to any portion of the antibody. Three functional groups in antibodies are the sites for covalent modifications: amines (—NH2), thiol groups (—SH) and carbohydrate residues (Shrestha D, et al, 2012). As such, any of the polymers disclosed herein may be coupled to amine residues, thiol residues, and carbohydrate residues or any combination thereof. In some embodiments, the polymers are coupled to Fc portions of the antibody. In other embodiments, the polymers are coupled to the hinge regions of the antibody. In some embodiments, the polymers are coupled to one or more of the Fc regions of the antibody and one or more of the hinge regions of the antibody. Indeed, any combination is contemplated by the present disclosure.

Amino group are generally favored primarily because of the abundance of these moieties in the antibody. Lysine, arginine and histidine are the three chief amino acids that contain amine side chains and constitute almost 10% of the total protein composition. However, the randomness of amino groups poses a risk that the antibody may become deactivated. (Adamczyk M, et al, 1999, Bioconjug Chem; Jeanson A, et al, 1988, J Immunol Methods; Vira S, et al, 2010, Anal Biochem; Pearson J E et al, 1998, Immunol Methods). In some embodiments, one or more polymers are coupled to amino groups of an antibody.

On the other hand, and under appropriate reaction conditions, sulfhydryl labeling offers high specificity targeting of the disulfide bonds between the two heavy chains of the antibody in the hinge region. Since the hinge region is distant from the antigen binding site, this modification is believed to better preserve antibody's binding affinity. The drawback, however, is the lower level of labeling (e.g.

usually less than 3 labels per antibody). In some embodiments, one or more polymers are coupled to thiol groups of an antibody.

Conjugations at the carbohydrate moieties present in the Fc part of the antibody are similar to that of thiol group, such that modification occurs at a —CHO group distant from the antigen binding site. Again, without wishing to be bound by any particular theory, it is believed that conjugation at the carbohydrate offers less of a negative impact on an antibody's binding affinity. The degree of labeling varies depending on the glycosylation status of a specific antibody. However, loss in antibody affinity was still reported by Jeanson A, et al, 1988, J Immunol Methods. In some embodiments, one or more polymers are coupled to carbohydrate groups of an antibody.

In some embodiments, multiple, different polymer-antibody conjugates (used as detection probes) may be used in a multiplexed assay to detect multiple targets within a tissue sample.

In some embodiments, the conjugates, and hence the target, may be directly detected (such as those labels comprising fluorescein or fluorescein derivatives). In other embodiments, the conjugates may be indirectly detected.

Detection Reagents

In embodiments where the polymer conjugates are detected indirectly, specific reagents are utilized to enable detection of the conjugate, and hence the target. In some embodiments, detection reagents are utilized which are specific to the Label of a polymer conjugate. In some embodiments, the detection reagents comprise a secondary antibody which is specific for the Label of the polymer conjugate, i.e. the secondary antibody is an anti-Label antibody. The secondary antibody may be conjugated to a "detectable moiety" to effectuate detection of the polymer conjugates.

In some embodiments, the detection reagents include "labeling conjugates" and "signaling conjugates" as described in US Patent Publication No. 2013/0260379, the disclosure of which is hereby incorporated by reference herein in its entirety.

Detectable Moieties

A "detectable moiety" is a molecule or material that can produce a detectable (such as visually, electronically or otherwise) signal that indicates the presence (i.e. qualitative analysis) and/or concentration (i.e. quantitative analysis) of the label in a sample. A detectable signal can be generated by any known or yet to be discovered mechanism including absorption, emission and/or scattering of a photon (including radio frequency, microwave frequency, infrared frequency, visible frequency and ultra-violet frequency photons).

In some embodiments, the detectable moiety may be selected from any of the agents enumerated as "labels" as identified herein. In other embodiments, the detectable moiety includes chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens (such as those enumerated as "labels" herein) that can be detected through antibody-hapten binding interactions using additional detectably labeled antibody conjugates, and paramagnetic and magnetic molecules or materials.

In other embodiments, the detectable moiety is an enzyme. For example, detection reagents may be utilized that are specific to the labels of the polymer conjugate and which themselves are conjugated to an enzyme (e.g. a labeling conjugate). As a specific example, a secondary antibody (e.g. an anti-Label antibody) may be conjugated to an enzyme, where the secondary antibody is specific to the Label. In some embodiments, suitable enzymes include, but are not limited to, horseradish peroxidase, alkaline phosphatase, acid phosphatase, glucose oxidase, β-galactosidase, β-glucuronidase or β-lactamase. In other embodiments, enzymes include oxidoreductases or peroxidases (e.g. HRP, AP). In these embodiments, the enzyme conjugated to the detection reagent (e.g. a labeling conjugate) catalyzes conversion of a chromogenic substrate (or signaling conjugate) to a reactive moiety which covalently binds to a sample proximal to or directly on the target.

Of course, the detectable moieties can themselves also be detected indirectly, e.g. if the detectable moiety is a hapten, then yet another antibody specific to that detectable moiety may be utilized in the detection of the detectable moiety, as known to those of ordinary skill in the art.

Detection Kits

In some embodiments, the conjugates of the present disclosure are part of a "detection kit." In general, any detection kit includes a conjugate (detection probe) and detection reagents (comprising a detectable moiety) for detecting the conjugate.

The detection kits may include a first composition comprising a conjugate (e.g. an antibody conjugate) and a second composition comprising detection reagents specific to that first composition, such that a target may be detected via the detection kit. In some embodiments, the detection kit includes more than one conjugates for detecting different targets, where each kit also includes detection reagents specific for each of the conjugates included within the kit.

Figure 5A:
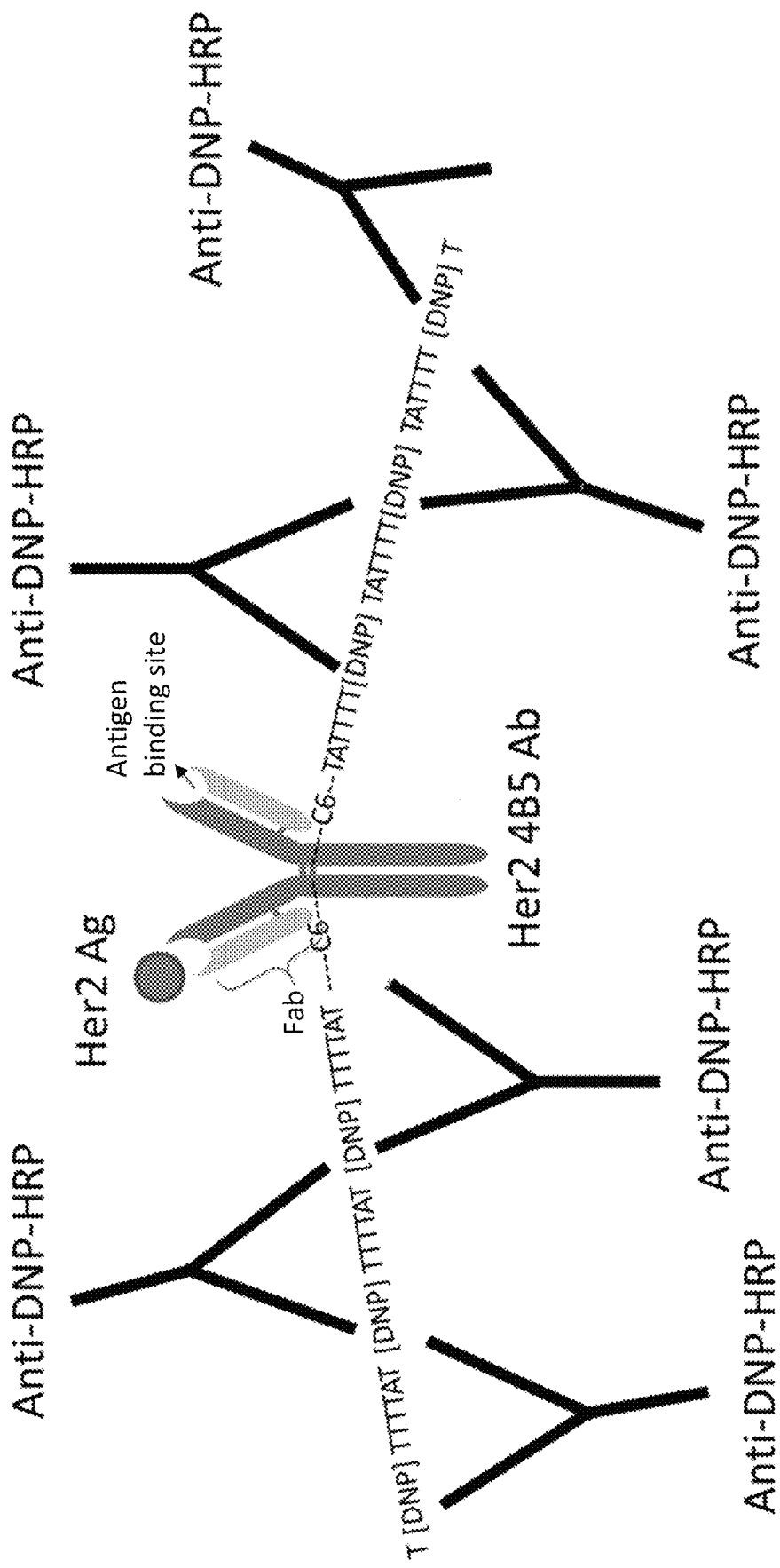
FIG. 5A sets forth a first detection scheme which utilizes conjugates and secondary antibodies to detect those conjugates, where the secondary antibodies comprise an enzyme.

By way of example, a kit may include an antibody conjugate specific for a first target having a first label (a first detection probe) and an antibody conjugate specific for a second target having a second label (a second detection probe), wherein the first and second labels are different. In this particular embodiment, while the antibodies and labels of the first and second detection probes may vary, the selection of the oligonucleotide, spacer, and/or linker of the conjugates may be the same or different, i.e. the polymer backbone for each conjugate may be the same or different. The kit may further comprise detection reagents specific for each of the detection probes. For example, if a label is an enzyme, a substrate for the enzyme may be included. On the other hand, and again by way of example only, if the label is a hapten, an anti-hapten antibody may be included within any kit to bind to the haptens, and where the anti-hapten antibody includes a detectable moiety for detection (see, for example, FIG. 5A).

Kits may include other agents, including buffers; counterstaining agents; enzyme inactivation compositions; deparrafinization solutions, etc. as needed for manual or automated target detection.

Detection Methods

The present disclosure also contemplates methods of detecting targets using any of the conjugates described herein. While certain embodiments may refer to the use of antibodies or antibody conjugates for immunohistochemistry, other specific binding entities are contemplated and may be used according to methods known to those of skill in the art (e.g. nucleic acids for in situ hybridization).

Figure 6:
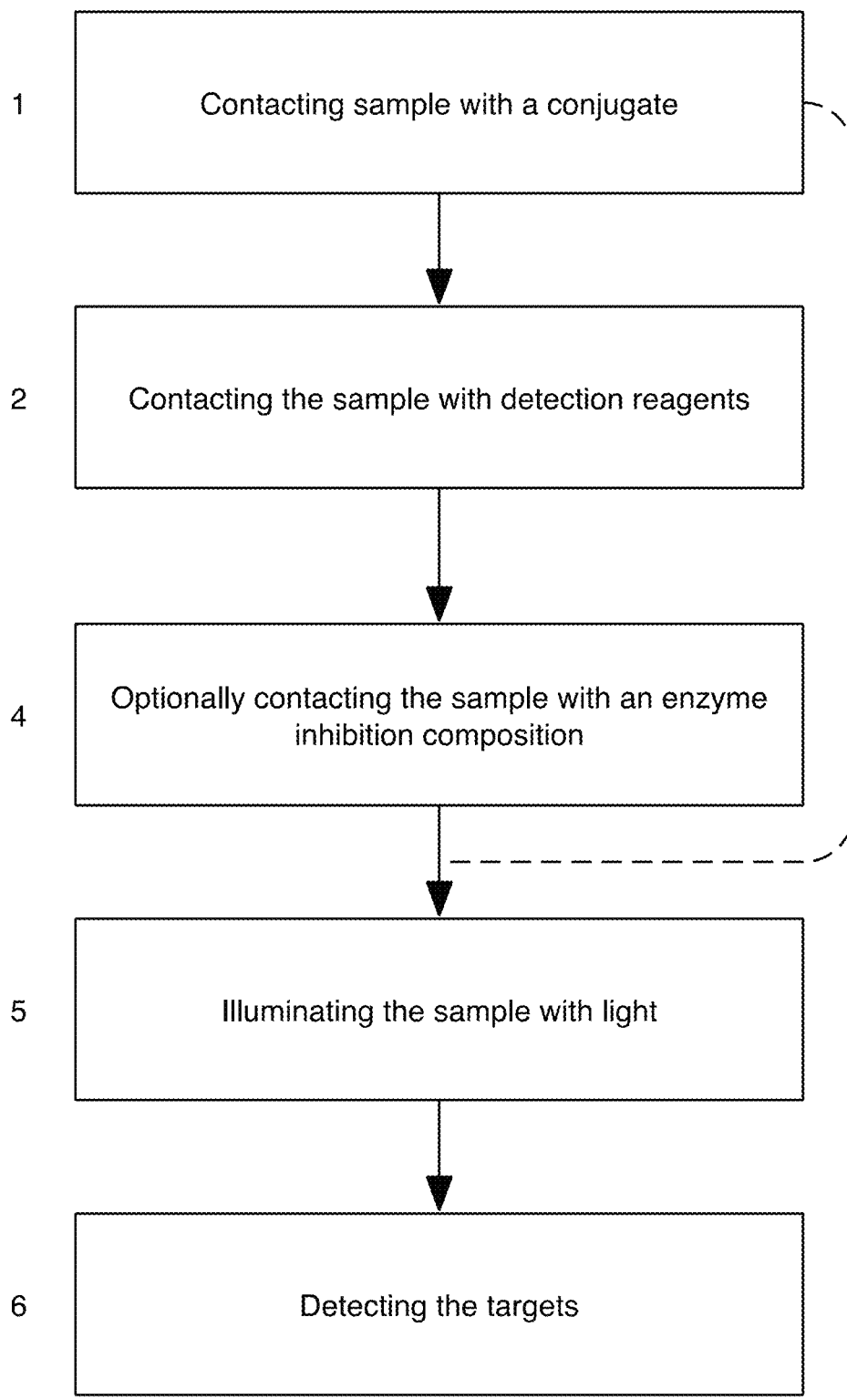
FIGS. 6 and 7 provide flow charts illustrating methods of using conjugates as detection probes for targets (singleplex or multiplex), where the detection probes are detected using detection reagents or labeling conjugates and signaling conjugates.
Figure 7:
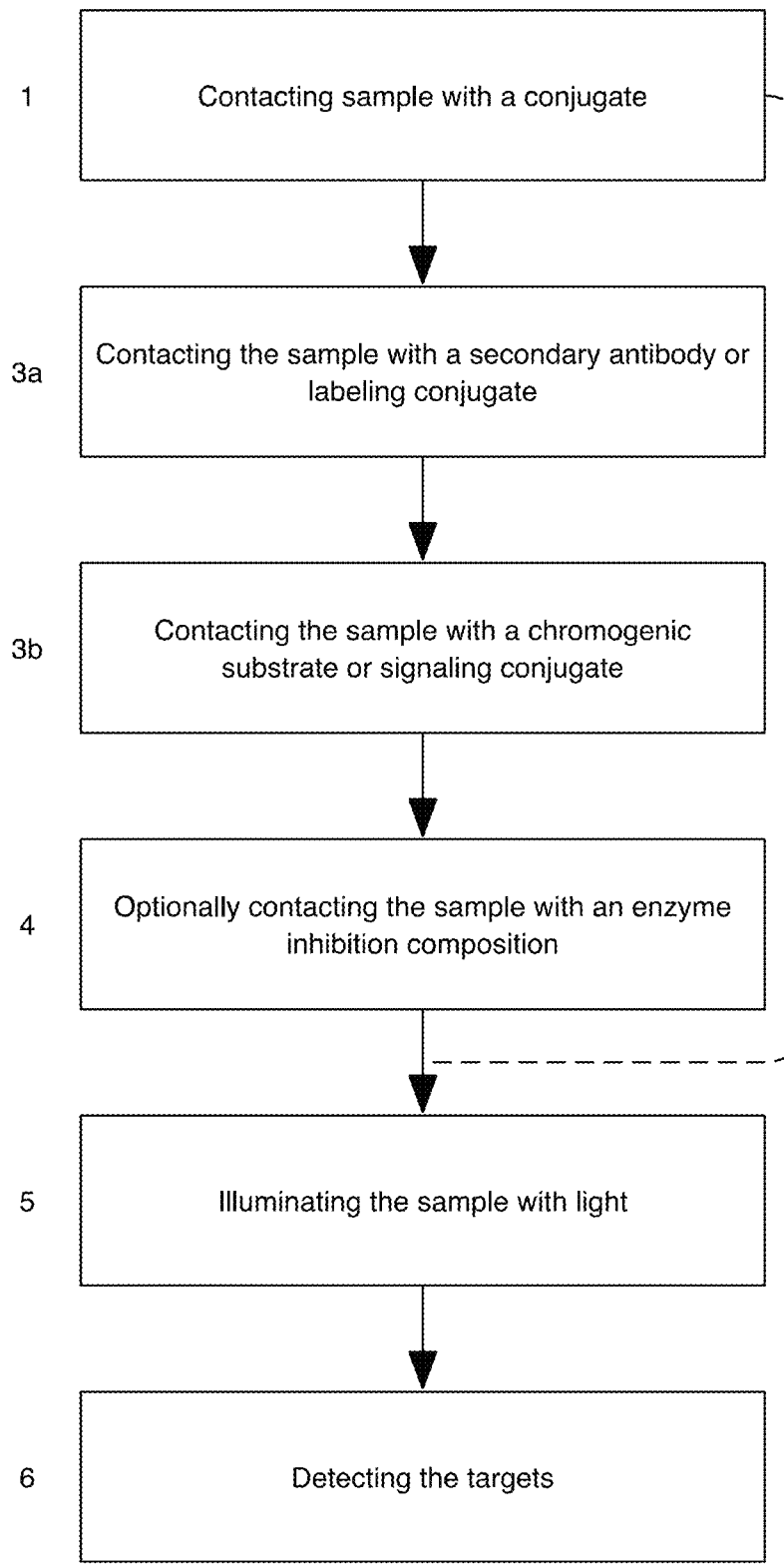

The present disclosure also provides for methods of multiplexed detection, including automated multiplex detection. FIGS. 6 and 7 provide illustrate flowcharts delineating the steps of certain embodiments of the methods of the present disclosure, where the conjugates comprise Labels which are indirectly detected. In particular, the method sets forth a sequential multiplex detection scheme where at step 1 the sample is contacted with a conjugate (detection probe) as disclosed herein. When the conjugate is introduced into the sample, it will form a conjugate target complex. A subsequent step 2 includes contacting the sample with detection reagents. The detection reagents may include labeling conjugates and chromogenic substrates or signaling conjugates as illustrated in steps 3a and 3b of FIG. 7. A further subsequent step 4 (optional) comprises contacting the sample with an enzyme inhibition composition. A dashed line indicates that the process of steps 1 through 4 may be repeated one or more times to provide for the sequential multiplex detection of targets within the tissue sample. The method also comprises a step 5 of illuminating sample with light and detecting the targets at step 6. While FIGS. 6 and 7 illustrate that all of the targets are detected simultaneously, the targets may be detected at any time during the multiplex method disclosed herein. Moreover, the multiplex detection assays of the present disclosure may be simultaneous of sequential. For example, each of the different conjugates may be added simultaneously or sequentially, but before any detection reagent is added. As another example, three conjugates may be sequentially applied at step 1, prior to introduction of any detection reagents.

As a further example of a multiplex assay according to the present disclosure, a first antibody conjugate specific to a first target comprising a first label is introduced to a sample. In some embodiments, the first antibody conjugate forms a detectable first target-antibody conjugate complex. Either simultaneously or subsequently, a second antibody conjugate specific to a second target comprising a second label is introduced to the sample to form a second target-antibody conjugate, where the first label on the first conjugate is different than the second label on the second conjugate. Third, fourth, and nth additional antibody conjugates specific to other targets (forming "n" target antibody-complexes) and having yet different labels may be further introduced, again either sequentially or simultaneously with the first and/or second antibody conjugates. After the antibody conjugate is deposited, it may be detected, either directly or indirectly depending, of course, on the label of the conjugate. In some embodiments, additional reagents are introduced to enable the detection of the target and the additional reagents include a detectable moiety, as described herein. In some embodiments, the label is a fluorescein may be directed detected. In other embodiments, if the label is an enzyme a substrate for the enzyme (a detectable moiety) may be introduced such that a colored precipitate may be detected. In yet other embodiments, an anti-label antibody (a secondary antibody) is introduced to elicit detection, where the anti-label antibody is specific to the label of the conjugate. For example, if the label is a hapten, an anti-hapten antibody specific to the hapten label is introduced, where the anti-hapten antibody comprises a detectable moiety. In some embodiments, the detectable moiety of the anti-hapten antibody is an enzyme, and a substrate for the enzyme is further introduced to detect the conjugate and target.

In the context of a multiplex assay where multiple chromogenic reagents are detected sequentially, and where the detection employs the use of enzymes, it is desirable to inactivate any reagent or endogenous enzymes between successive detection steps. As a result, it is believed that enzymes present in any one detection step will not interfere with those in a later detection steps. This in turn is believed to improve upon the visualization and detection of the different detectable moieties used in the multiplex assay. Any enzyme inactivation composition known in the art may be used for this purpose. In some embodiments, an enzyme inactivation composition is applied to inactivate the reagent or endogenous enzymes after each detection step. Exemplary enzyme inactivation compositions are disclosed in U.S. application 62/159,297, the disclosure of which is incorporated by reference herein in its entirety.

In some embodiments, a denaturation step prevents the enzyme used in a first set of detection reagents from acting on a second substrate. In some embodiments, the denaturant is a substance that denatures the enzyme in the first detection reagent set. In some embodiments, the denaturant is, for example, formamide, an alkyl-substituted amide, urea or a urea-based denaturant, thiourea, guanidine hydrochloride, or derivatives thereof. Examples of alkyl-substituted amides include, but are not limited to, N-propylformamide, N-butylformamide, N-isobutylformamide, and N,N-dipropylaformamide. In some embodiments, the denaturant is provided in a buffer. For example, formamide may be provided in a hybridization buffer comprising 20 mM dextran sulfate (50-57% % formamide (UltraPure formamide stock), 2×SSC (20×SSC stock containing 0.3 M citrate and 3M NaCl), 2.5 mM EDTA (0.5M EDTA stock), 5 mM Tris, pH 7.4 (1 mM Tris, pH 7.4 stock), 0.05% Brij-35 (10% stock containing polyoxyethylene (23) lauryl ether), pH 7.4. In some embodiments, the sample is treated with the denaturant for a period of time and under conditions sufficient to denature the first target probe detection enzyme, for example alkaline phosphatase. In some embodiments, the sample is treated with the denaturant for about 15 to about 30 minutes, preferably about 20 to 24 minutes at about 37° C. In some embodiments, the sample is treated with the denaturant for a period of time and under conditions sufficient to denature the target enzyme while preserving hybridization of the second nucleic acid probe to the target.

Figure 5B:
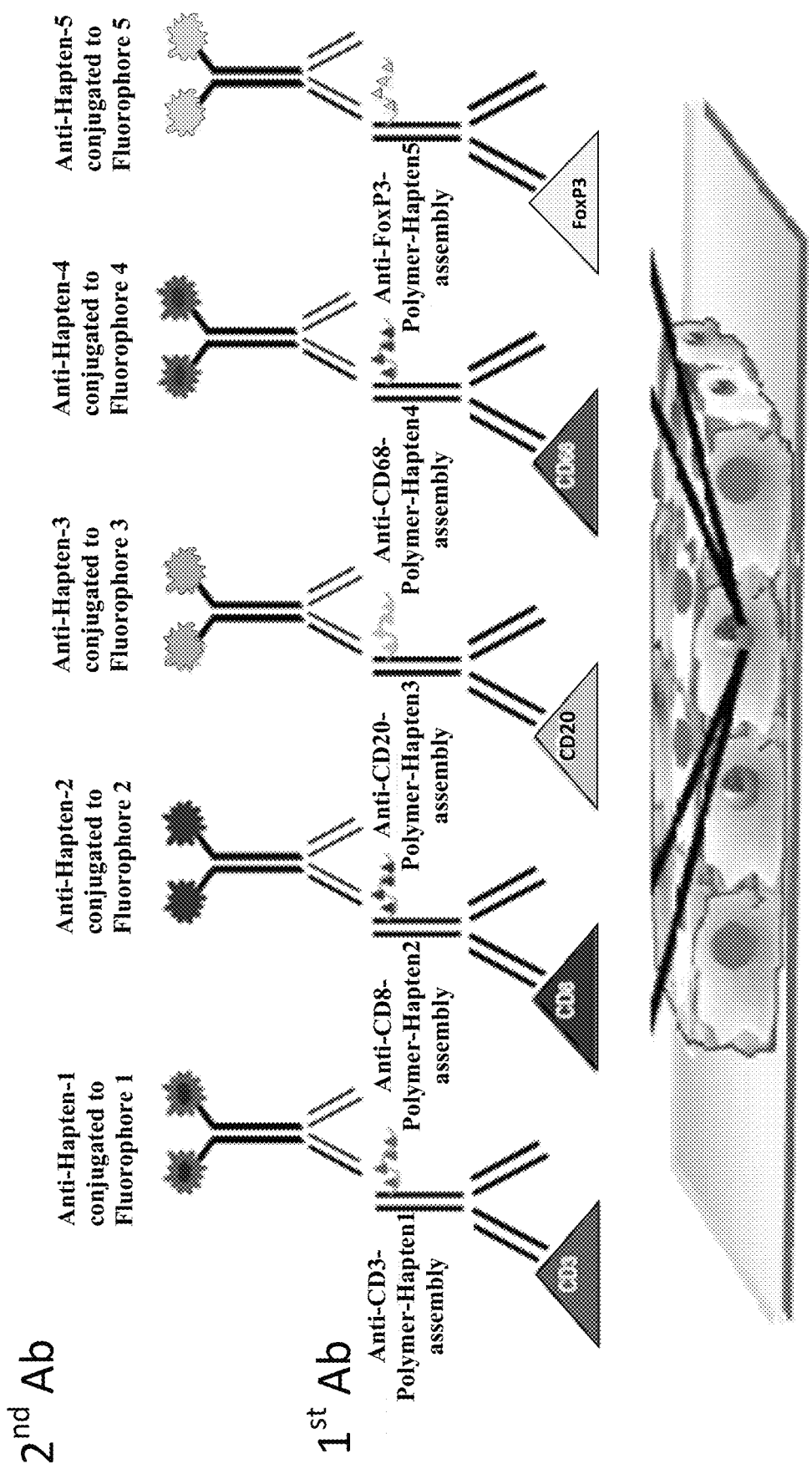
FIG. 5B sets forth a first detection scheme which utilizes conjugates and secondary antibodies to detect those conjugates, where the secondary antibodies comprise a fluorophore.

In another embodiment, and with reference to FIG. 5B, the illustrated embodiment depicts selecting a target, such as CD3 as a first target. An anti-CD3-polymer hapten1 conjugate is added to the sample to associate with the CD3 target. A secondary anti-hapten1 antibody (detection reagent) is applied to the sample to associate with hapten1. The secondary anti-hapten1 also includes a fluorophore coupled thereto (detectable moiety) that fluoresces at a known wavelength, thereby serving as a target identifier, allowing visualization of the assembled antibody-polymer hapten1 complex associated with the CD3 target. While the embodiment of FIG. 5B, illustrates that four haptens are utilized, any number of haptens may be incorporated, as disclosed herein.

This process can continue in a multiplexed assay. FIG. 5B illustrates using anti-CD8-polymer hapten2 antibodies for detecting CD8; anti-CD20-polymer hapten3antibodies for detecting CD20; anti-CD68-oligonucleotide hapten4 antibodies for detecting CD68; and antiFoxP3-polymer hapten5 antibodies for detecting FoxP3. The required reagents for antibody-detectable moiety assembly in a multiplexed assay can be applied simultaneously to a sample, or sequentially, either using a manual assay or using an automated staining device.

The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

In some embodiments if the specimen is a sample embedded in paraffin, the sample can be deparaffinized using appropriate deparaffinizing fluid(s). After a waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

After the specimens are processed, a user can transport specimen-bearing slides to an imaging apparatus for analysis or other downstream processing. For example, the imaging apparatus may be a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entities. In other embodiments, the imaging apparatus includes a digital camera coupled to a microscope.

Synthesis

Figure 8:
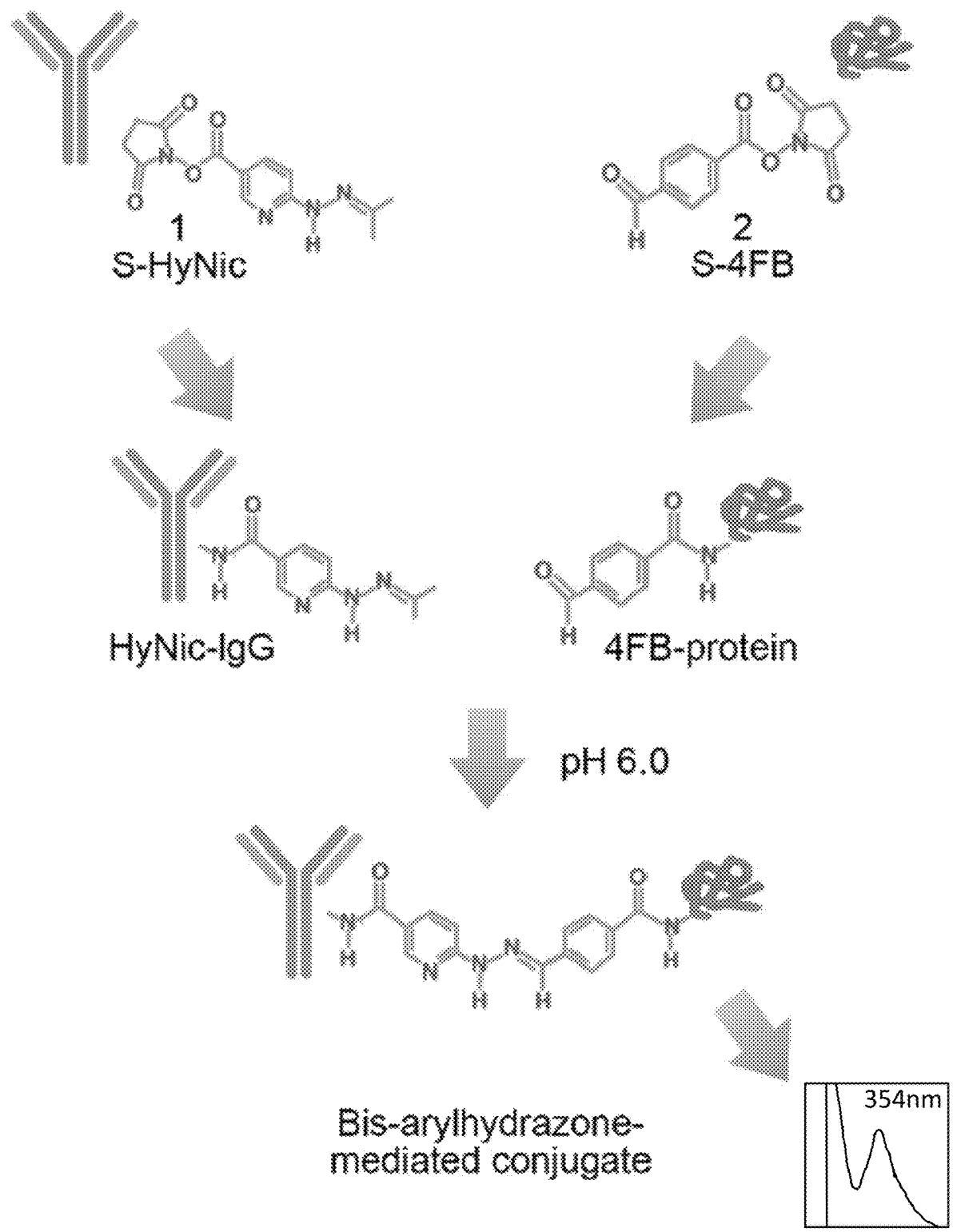
FIG. 8 illustrates one method of coupling a polymer (comprising an oligonucleotide) to an antibody to form the respective polymer-antibody conjugate.

The present disclosure provides exemplary embodiments of a method for making polymer-antibody conjugates. Appropriate conjugation methods also will be generally known to a person of ordinary skill in the art. See, for example, U.S. patent application No. 2013/0184184, which is incorporated herein by reference. For certain exemplary embodiments, conjugation can be accomplished at the hinge or Fc region of an antibody. Disulfide bonds in the hinge region of the antibody can be reduced selectively, typically using mild reduction using DTT. The resulting sulfhydryl bonds are then labeled, such as with maleimide-dPEG8-hapten ester linker. Solely by way of example, one method for forming polymer-antibody conjugates is illustrated below in Scheme 1. The method generally comprises reacting an antibody 2 with 5-HyNic 4 to form a 5-HyNic-antibody conjugate 6. Separately, a 3'- or 5'-amino modified oligonucleotide (which is part of the polymer) 8 is reacted with S-4FB 10 to form an 4FB-polymer 12. The 5-HyNic-antibody conjugate 6 is then coupled to the 4FB-oligo 12 in the presence of a catalyst to form a conjugate 14 comprising an antibody coupled to an oligonucleotide part of the polymer by a bus-aryl hydrazine. An alternative synthetic scheme is shown in FIG. 8.

Scheme 1: Synthetic method of coupling an antibody to a polymer of the present disclosure to provide a polymer-antibody conjugate.

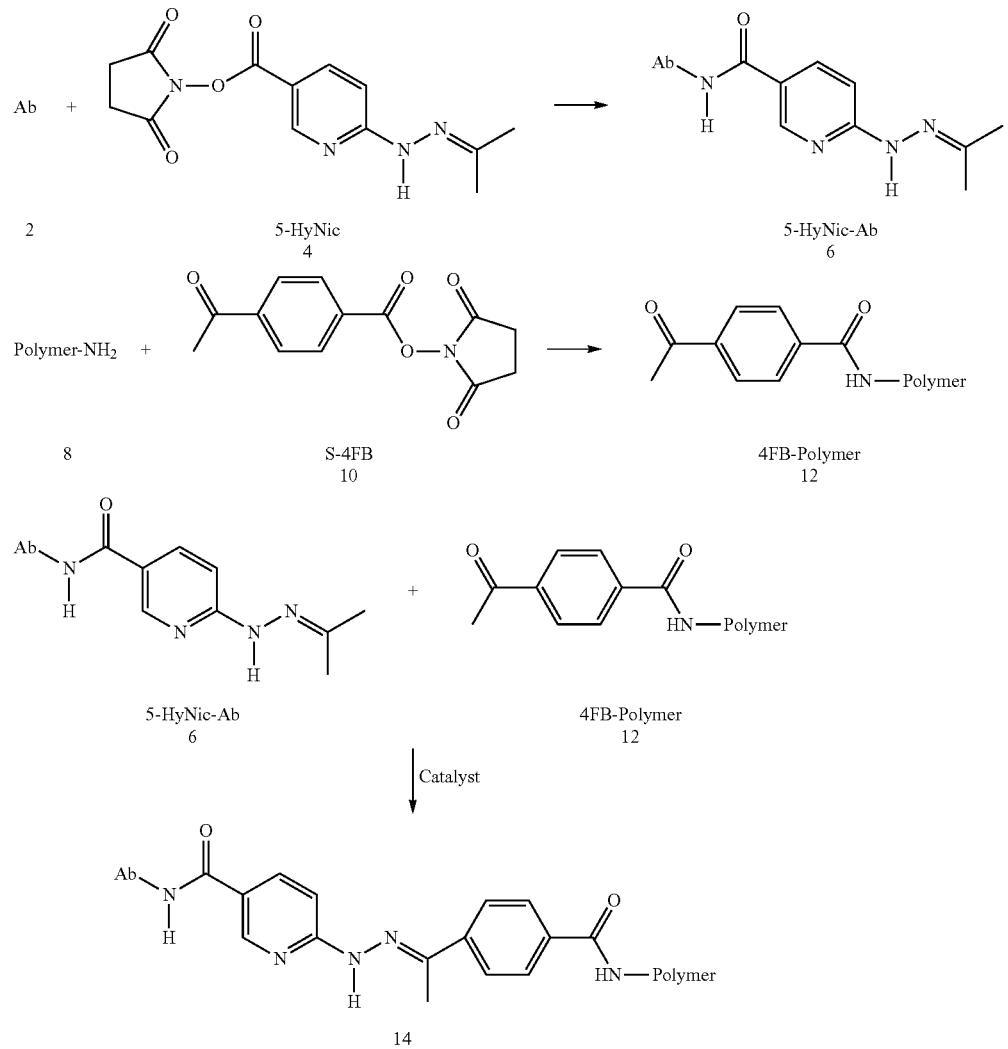

In certain embodiments, the antibody which is conjugated to the polymers of Formula (I) may be a monoclonal antibody directed against a specific antigen of interest. The monoclonal antibody may be conjugated to a polymer, such as those of Formula (I), to form a conjugate. A polymer having a suitable terminal reactive group (e.g. an amino group), for example, may be prepared using solid phase phosphoramidite chemistry. The N-hydroxysuccinimide of sulfo-succinimidyl activated 4-formyl benzoate (S-4FB) may be used to modify and activate the polymer (e.g. the [Olig] portion of the polymer). Alternatively, polymers comprising oligonucleotides may be prepared using solid phase phosphoramidite chemistry with a terminal 4FB phosphoramidite monomer. The oligonucleotide backbone of the polymer may have different lengths, different chemistries, for example to incorporate alternative backbones, bases, or inert linkers, or geometries. Further, the 4FB moiety might be incorporated by a number of alternative chemistries or by biochemical means using enzymes. An 4FB moiety may be placed at either the 3'- or 5'-end, or in the middle or close to either end of, an oligonucleotide.

In parallel, the antibody or other protein, biomolecule, nucleic acid, or other probe, would be synthesized to incorporate one or more HyNic moieties via reaction of the N-hydroxysuccinimide of sulfo-succinimidyl activated 6-hydrazinopyridine-3-carboxylate (SHyNic) with a primary amine, such as a Lysine amino acid epsilon amino group, which are prevalent on the surface of proteins. Excess equivalents of S-HyNic to each mole equivalent of antibody might be used. Purified 4FB-modified polymer (above) and HyNic-modified antibody are combined, typically using a molar excess of the polymer to the antibody. A bisarylhydrazone bond forms to provide the antibody-polymer conjugate. Conjugation of a plurality of polymers, as disclosed herein, to the antibody can be determined by electrophoresis. The process yields a mixture of HyNic-modified antibody, 4FB-polymer and antibody-polymer conjugates with one or more polymers coupled to each antibody. By varying the mole ratio of S-HyNic to antibody and of 4FB-modified polymer to HyNic modified antibody, essentially all, or nearly all, of the antibody can be converted to the respective conjugate. The antibody-polymer conjugate may be isolated, such as by using magnetic affinity beads.

The stoichiometry of the conjugation reaction to form the antibody-polymer conjugates may comprise one equivalent of modified antibody and at least 0.5 equivalents of modified polymer. A person of ordinary skill in the art will appreciate that the stoichiometry can be other than that, such as, for example, at least 1.0 equivalent, at least 1.5 equivalents, at least 2.0 equivalents, at least 2.5 equivalents, at least 3.0 equivalents, at least 3.5 equivalents, or at least 4.0 equivalents of polymer to antibody. The number of polymers per antibody also can be adjusted as desired. Without being limited to a particular theory of operation, it currently is believed that best results will be obtained by limiting the number of oligonucleotides per antibody to preserve antibody function.

Antibody-polymer conjugates may be purified using any suitable means, such as by binding the antibody-polymer conjugates to a column comprising agarose and metal ions immobilized within the stationary phase of the column (which may be called "magnetic agarose" or "magnetic affinity beads"). Antibody-polymer conjugates may include moieties, such as histidine rich regions, that bind to metal ions immobilized on a stationary phase. This process may be used to separate excess modified polymer, which does not have functionality that may bind to the metal ions in a similar chelating fashion. Excess modified polymers are washed by a series of elutions, and bound antibody-polymer conjugates released by eluting with a displacing agent, such as, for example, EDTA.

Oligonucleotides, comprising the polymers of the present disclosure, may be prepared according to any method known to those of ordinary skill in the art. For example, solid phase synthesis may be used, where the 3'-nucleoside of the oligonucleotide being synthesized is attached. The oligonucleotide synthesis starts with the 3' base. During the synthesis cycle the oligonucleotide is elongated toward the 5' end. For each coupling step, the nucleotide is delivered as a nucleoside phosphoramidite where a reactive phosphoramidite group is located at the 3'-OH and the 5'-OH is modified with a dimethoxytrityl protection group (DMT). The reactive phosphoramidite group reacts with the 5'-OH of the attached oligonucleotide. In general, oligonucleotide synthesis cycle comprises the following steps: Detritylation (the cleavage of the DMT protecting group from the previous base to form a 5' reactive hydroxyl function); Coupling (the 5'-OH group reacts with added activated phosphoramidite bearing the next base and, as a result, both nucleosides are linked together); Capping (any free 5'-OH groups which did not couple to the next nucleotide have to be excluded from the next coupling steps; acetylation is used in the capping step to block all reactive 5'-OH groups); and Oxidation (the nucleotides are linked via phosphorous containing bonds that have been created in the coupling step where the phosphorus group is oxidized using iodine solution). After the oxidation step a new synthesis cycle starts to add the next nucleotide. The cycle is repeated until the desired sequence is synthesized. After the synthesis has been performed and the desired length has been reached, the oligonucleotide undergoes one last detritylation reaction. The oligonucleotide is then cleaved from the solid support and the remaining protecting groups are cleaved to yield a biologically functional oligonucleotide.

Oligonucleotides, once synthesized, can be modified in several different ways by utilizing the active groups of the nucleotide or creating nucleotide analogues. Oligonucleotide modifications are often necessary for coupling to an appropriate spacer, or other polymer backbone component as provided herein. The most common oligonucleotide modifications are set forth below:

Terminal modifications utilizing the 3' and 5' OH groups (e.g., C6 and C7 amino modifiers, biotin-ON, biotin-TEG, cholesterol-TEG, fluorescein, thiol modifications, phosphate);

Base modifications (e.g., 5-bromo-dU, 5-bromo-dC, 5-fluoro-dU, deoxyinosine, 5-iodo-dC, 5-iododU, 5-methyl-dC, 5-nitroindole, deoxyuridine);

Thymidine analogues, replacing a T residue in the sequence (e.g., C2 dT and C6 dT amino modifiers, biotin-dT, dabcyl-dT, fluorescein-dT, TAMRA-dT);

Post-synthesis modifications (By choosing the appropriate amino modifier, these modifications can be attached in different positions in the oligonucleotide);

Modifications of the phosphate group (e.g., phosphorothioation); and

2' Modifications (2-O-methyl A/C/G/U, ribo A/C/G/U).

In some embodiments, terminal 5' modifications are made to incorporate functionality such that the oligonucleotide (and polymer, once fully synthesized) may be conjugated to a specific binding entity (e.g. addition of an AminoC6 group). Likewise, terminal 3' modifications are made to incorporate functionality such that the oligonucleotide may be coupled to a linker (comprising a label) or a spacer. The 5' and/or 3' modifications may be made during oligonucleotide synthesis or post-synthesis.

Modified oligonucleotides may be prepared by any suitable means. For example, modified oligonucleotides may be prepared by: suspending an amino-oligonucleotide in a suitable buffer; determining the oligonucleotide concentration, such as by spectrophotometric measurement; and reacting the modified oligonucleotide with, for example, with S-4FB, using a suitable solvent, such as dimethylformamide (DMF). The reaction mixture may be concentrated and the modified-oligonucleotide (4FB-modified oligonucleotide) concentration measured by spectrophotometer measurement.

In some embodiments, the solid phase synthesis of the oligonucleotide may also include the direct incorporation of a linker or spacer during the solid phase oligonucleotide synthesis.

In some embodiments, a label is coupled to the oligonucleotide of the polymer via a linker, without the use of a spacer. For example, a DNP hapten (coupled to a linker) may be coupled to an oligonucleotide by the processes illustrated in schemes 2 and 3 herein.

Scheme 2: Process of coupling a DNP hapten (with a PEG linker) to an oligonucleotide, where no spacer is incorporated into the polymer backbone.

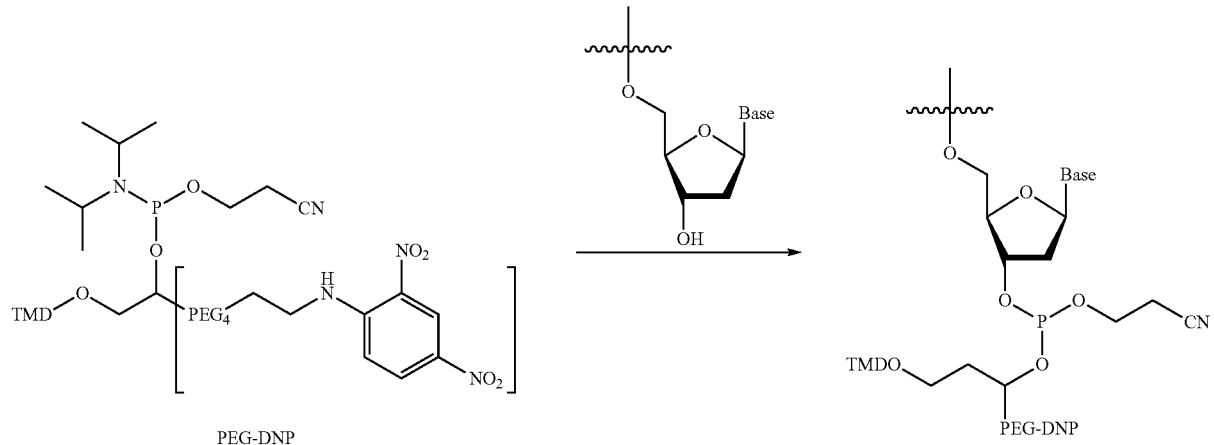

Scheme 3: Process of coupling a DNP hapten (with an ACA linker) to an oligonucleotide, where no spacer is incorporated into the polymer backbone.

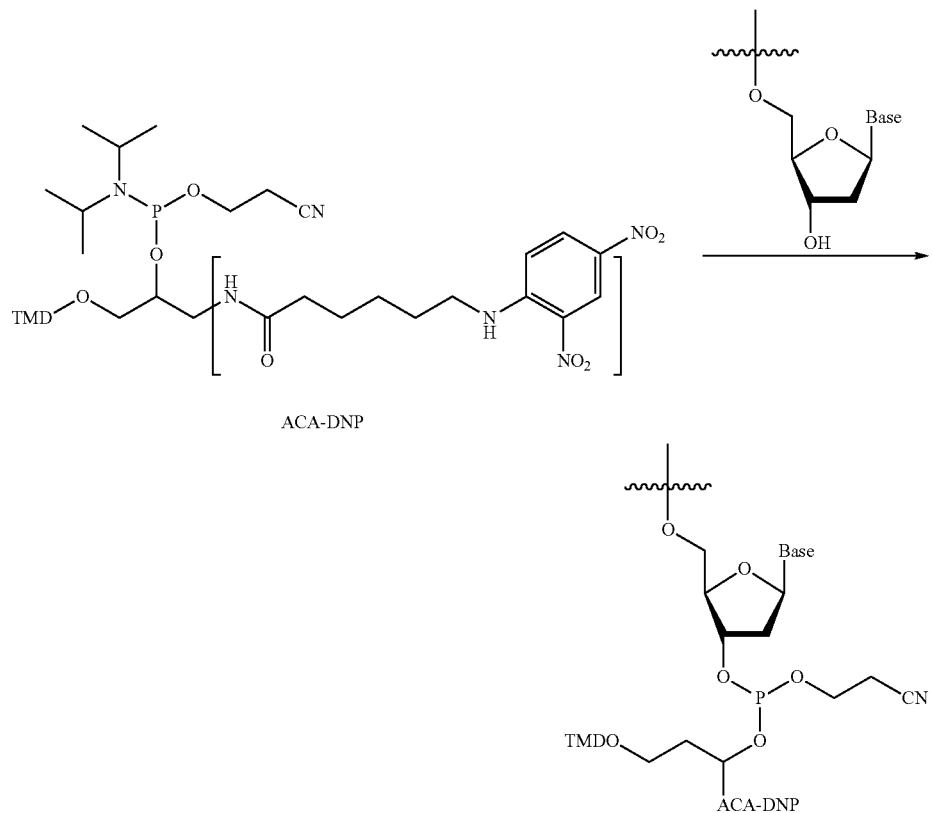

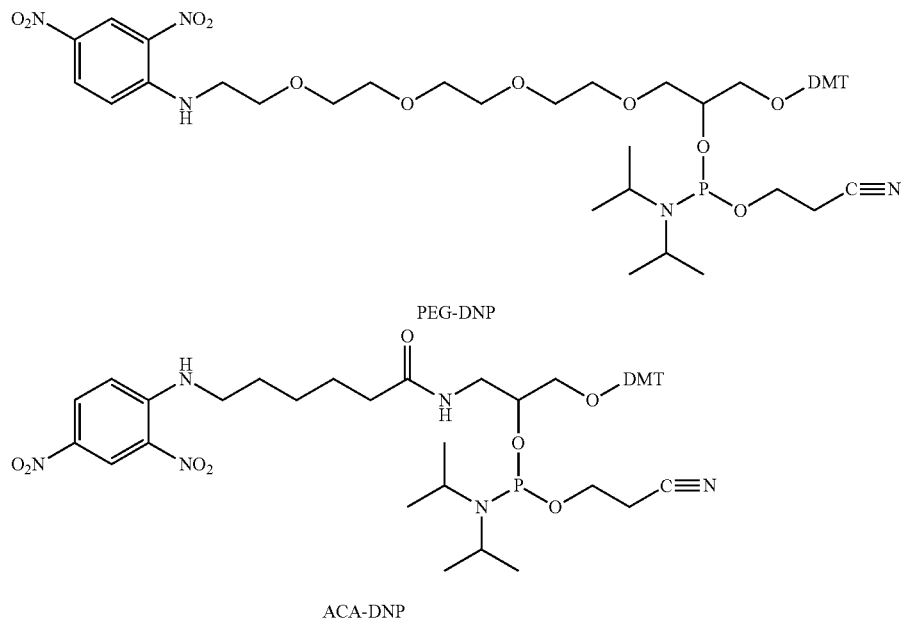

PEG-DNP

ACA-DNP

Hapten-linker conjugates have been formed using PEG-based linkers. One example of such a compound is shown below. The carboxylic acid functional group of the structure below may be converted to other reactive functional groups in working embodiments. For example, the carboxylic acid functional group can be converted to an activated ester, such as an NHS ester, as shown below. And, the activated ester can be converted to other useful reactive functional group, such as a hydrazide, as illustrated below.

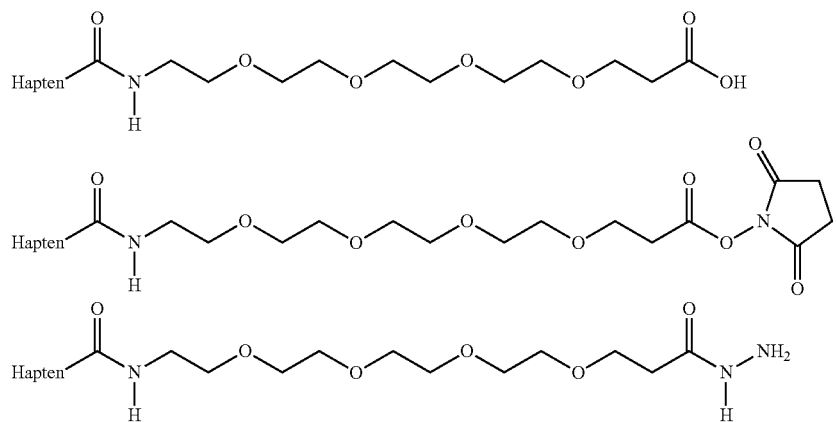

Spacers may be coupled to an oligonucleotide in the same manner (e.g. using similarly functionalized spacers) as shown above for linkers. In other embodiments, pre-synthesized oligonucleotides and pre-synthesized spacers may be reacted together, in the presence of a suitable catalyst or heat, to form the desired [olig]-[spacer] polymer backbone (see Spacer 9 and Spacer 18 below which comprise an oligonucleotide coupled to a PEG spacer). Alternatively, the "Spacer 9" and "Spacer 18" backbones shown below may be coupled to the Linker/Label components (above) using the steps outlined herein. Suitable methods are known to those of skill in the art. Labels coupled to linkers may then be attached to the [olig]-[spacer].

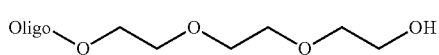

Spacer 9

-continued

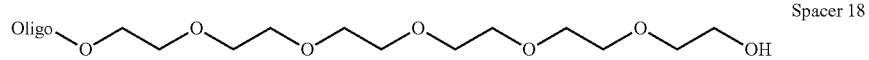
Spacer 18

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example, a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLT-SCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™

Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (1p32-p31; e.g., GENBANK™ Accession No. NC-000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FL|1 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (1p36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (1p34.2; e.g., GENBANK™ Accession No. NC-000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum, Entamoeba histolytica*, and *Giardia lamblia*, as well as *Toxoplasma, Eimeria, Theileria*, and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC-001460), human adenovirus B (NC-004001), human adenovirus C(NC-001405), human adenovirus D (NC-002067), human adenovirus E (NC-003266), human adenovirus F (NC-001454), human astrovirus (NC-001943), human BK polyomavirus (V01109; GI:60851) human bocavirus (NC-007455), human coronavirus 229E (NC-002645), human coronavirus HKU1 (NC-006577), human coronavirus NL63 (NC-005831), human coronavirus OC43 (NC-005147), human enterovirus A (NC-001612), human enterovirus B (NC-001472), human enterovirus C(NC-001428), human enterovirus D (NC-001430), human erythrovirus V9 (NC-004295), human foamy virus (NC-001736), human herpesvirus 1 (Herpes simplex virus type 1) (NC-001806), human herpesvirus 2 (Herpes simplex virus type 2) (NC-001798), human herpesvirus 3 (Varicella zoster virus) (NC-001348), human herpesvirus 4 type 1 (Epstein-Barr virus type 1) (NC-007605), human herpesvirus 4 type 2 (Epstein-Barr virus type 2) (NC-009334), human herpesvirus 5 strain AD 169 (NC-001347), human herpesvirus 5 strain Merlin Strain (NC-006273), human herpesvirus 6A (NC-001664), human herpesvirus 6B (NC-000898), human herpesvirus 7 (NC-001716), human herpesvirus 8 type M (NC-003409), human herpesvirus 8 type P (NC-009333), human immunodeficiency virus 1 (NC-001802), human immunodeficiency virus 2 (NC-001722), human metapneumovirus (NC-004148), human papillomavirus-1 (NC-001356), human papillomavirus-18 (NC-001357), human papillomavirus-2 (NC-001352), human papillomavirus-54 (NC-001676), human papillomavirus-61 (NC-001694), human papillomavirus-cand90 (NC-004104), human papillomavirus RTRX7 (NC-004761), human papillomavirus type 10 (NC-001576), human papillomavirus type 101 (NC-008189), human papillomavirus type 103 (NC-008188), human papillomavirus type 107 (NC-009239), human papillomavirus type 16 (NC-001526), human papillomavirus type 24 (NC-001683), human papillomavirus type 26 (NC-001583), human papillomavirus type 32 (NC-001586), human papillomavirus type 34 (NC-001587), human papillomavirus type 4 (NC-001457), human papillomavirus type 41 (NC-001354), human papillomavirus type 48 (NC-001690), human papillomavirus type 49 (NC-001591), human papillomavirus type 5 (NC-001531), human papillomavirus type 50 (NC-001691), human papillomavirus type 53 (NC-001593), human papillomavirus type 60 (NC-001693), human papillomavirus type 63 (NC-001458), human papillomavirus type 6b (NC-001355), human papillomavirus type 7 (NC-001595), human papillomavirus type 71 (NC-002644), human papillomavirus type 9 (NC-001596), human papillomavirus type 92 (NC-004500), human papillomavirus type 96 (NC-005134), human parainfluenza virus 1 (NC-003461), human parainfluenza virus 2 (NC-003443), human parainfluenza virus 3 (NC-001796), human parechovirus (NC-001897), human parvovirus 4 (NC-007018), human parvovirus B19 (NC-000883), human respiratory syncytial virus (NC-001781), human rhinovirus A (NC-001617), human rhinovirus B (NC-001490), human spumaretrovirus (NC-001795), human T-lymphotropic virus 1 (NC-001436), human T-lymphotropic virus 2 (NC-001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Imaging

Certain aspects, or all, of the disclosed embodiments can be automated, and facilitated by computer analysis and/or image analysis system. In some applications, precise color ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color can be measured in several different ways. For example, color can be measured as red, blue, and green values; hue, saturation, and intensity values; and/or by measuring a specific wavelength or range of wavelengths using a spectral imaging camera.

One disclosed embodiment involves using brightfield imaging with chromogenic dyes. White light in the visible spectrum is transmitted through the dye. The dye absorbs light of certain wavelengths and transmits other wavelengths. This changes the light from white to colored depending on the specific wavelengths of light transmitted.

The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Example 1

Staining for HER2 protein with anti-HER-2/neu (4B5) rabbit antibody and the HER2 4B5 rabbit antibody randomly labeled with the polymers of Formula Xb on amino residues were performed on a BenchMark ULTRA automated stainer. Briefly, approximately 4 mm-thick-unstained breast tumor sections case were cut onto SuperFrost Plus glass slides. The BenchMark ULTRA automated stainer includes online deparaffinization at about 72° C. and antigen retrieval (about 95° C. for about 36 min). Anti-HER-2/neu (4B5) rabbit antibody (about 6 ug/ml) or the rabbit anti-HER-2/neu (4B5) antibody were randomly labeled with a polymers of Formula Xb (1 ug/ml) were incubated for about 12 minutes at about 37° C. For anti-HER-2/neu (4B5) antibody, antigen detection was performed with about 25 ug/ml of goat anti-rabbit antibody labeled with horseradish peroxidase (HRP). For the anti-HER-2/neu (4B5) antibody randomly labeled with polymers of Formula Xb on amino residues, about 0.5-1.0 mg/ml of fish DNA was bulked as blocking reagent. Antigen detection was performed with about 10 ug/ml of a mouse anti-DNP-HRP antibody. Diaminobenzidine (DAB) was used as the chromogen, and Hematoxylin was used as the counterstain. Each separate tissue section was then scored for 4B5 staining on a 0-3+ intensity scale (1+=weak and incomplete membrane staining, 2+=moderately intense and complete membrane staining, and 3+=strong/intense and complete membrane staining).

Figure 9:
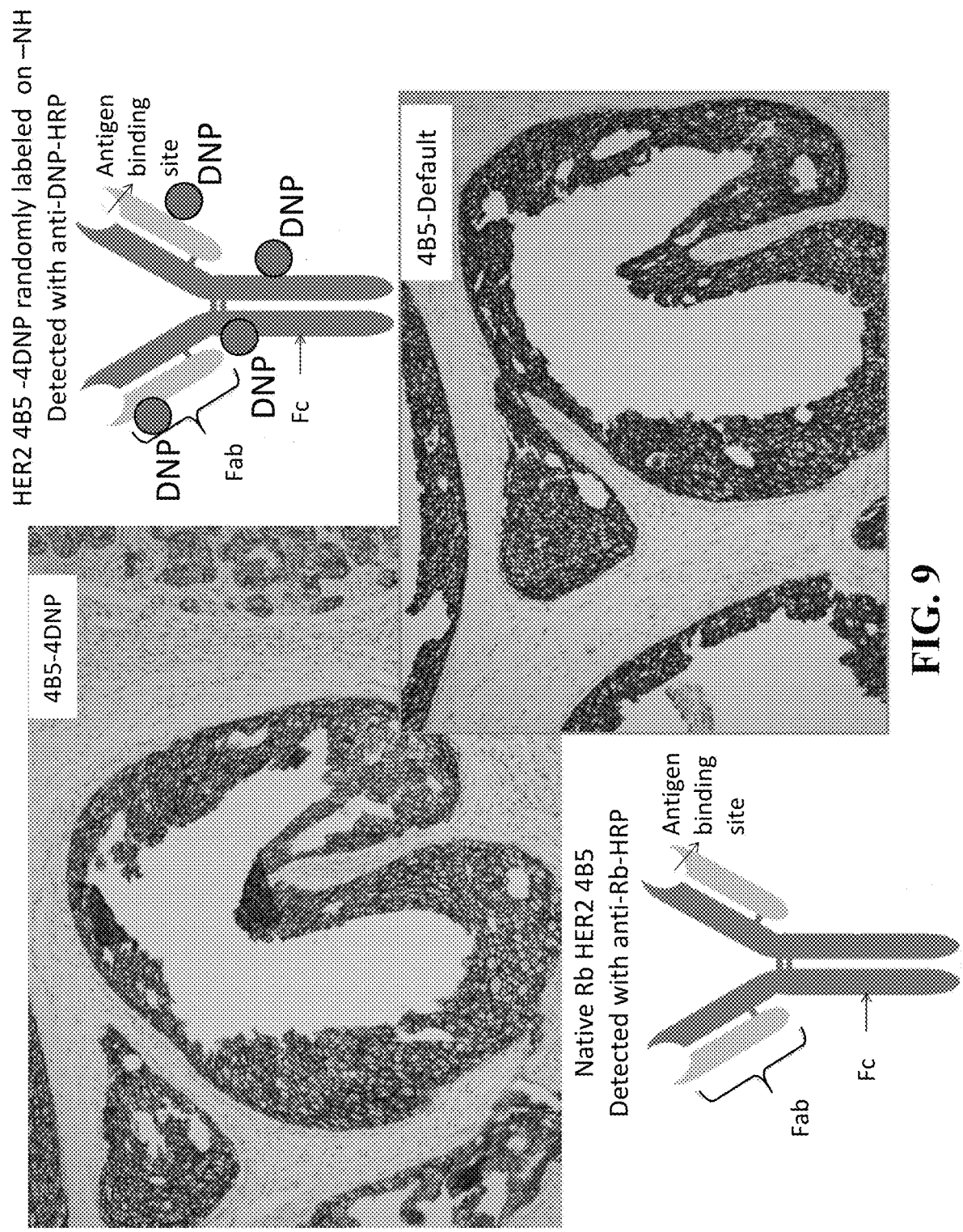
FIGS. 9, 10, and 11 compare the results of IHC staining assays, where native Rb HER2 4b5 antibodies and HER2-antibody-conjugates are used.

The HER2 4B5-4DNP randomly labeled with polymers of Formula Xb stained weaker than the native HER2 4B5 antibody (see FIG. 9). Without wishing to be bound by any particular theory, it is possible that the labeled antibody has compromised affinity due to random labeling on the lysine residues in CDR.

Example 2

Staining for HER2 protein with anti-HER-2/neu (4B5) rabbit antibody and the HER2 4B5 rabbit antibody labeled with polymers of Formula Xd on thiol residues at the hinge region were performed on a BenchMark ULTRA automated stainer. Briefly, approximately 4 mm-thick-unstained breast tumor sections were cut onto SuperFrost Plus glass slides. The BenchMark ULTRA automated stainer includes online deparaffinization at about 72° C. and antigen retrieval (about 95° C. for about 36 min). Anti-HER-2/neu (4B5) rabbit antibody (about 6 ug/ml) or the rabbit anti-HER-2/neu (4B5) antibody labeled with polymers of Forumla Xd on thiol residues at the hinge region (about 1 ug/ml) were incubated for about 12 minutes at about 37° C. For the anti-HER-2/neu (4B5) antibody, antigen detection was performed with about 25 ug/ml of goat anti-rabbit antibody labeled with horseradish peroxidase (HRP) (prepared from ULTRAVIEW UNIVERSAL DAB DETECTION KIT, 760-500). For the anti-HER-2/neu (4B5) antibody labeled with polymers of Formula Xd on thiol residues at the hinge region, about 0.5-1.0 mg/ml of fish DNA was bulked as blocking reagent. Antigen detection was performed with about 10 ug/ml of a mouse anti-DNP-HRP antibody (prepared from DISCOVERY anti-DNP HRP Multimer RUO, 760-4821). Diaminobenzidine (DAB) was used as the chromogen, and Hematoxylin was used as the counterstain. Each separate tissue section was then scored for 4b5 staining on a 0-3+ intensity scale (1+=weak and incomplete membrane staining, 2+=moderately intense and complete membrane staining, and 3+=strong/intense and complete membrane staining).

Figure 10:
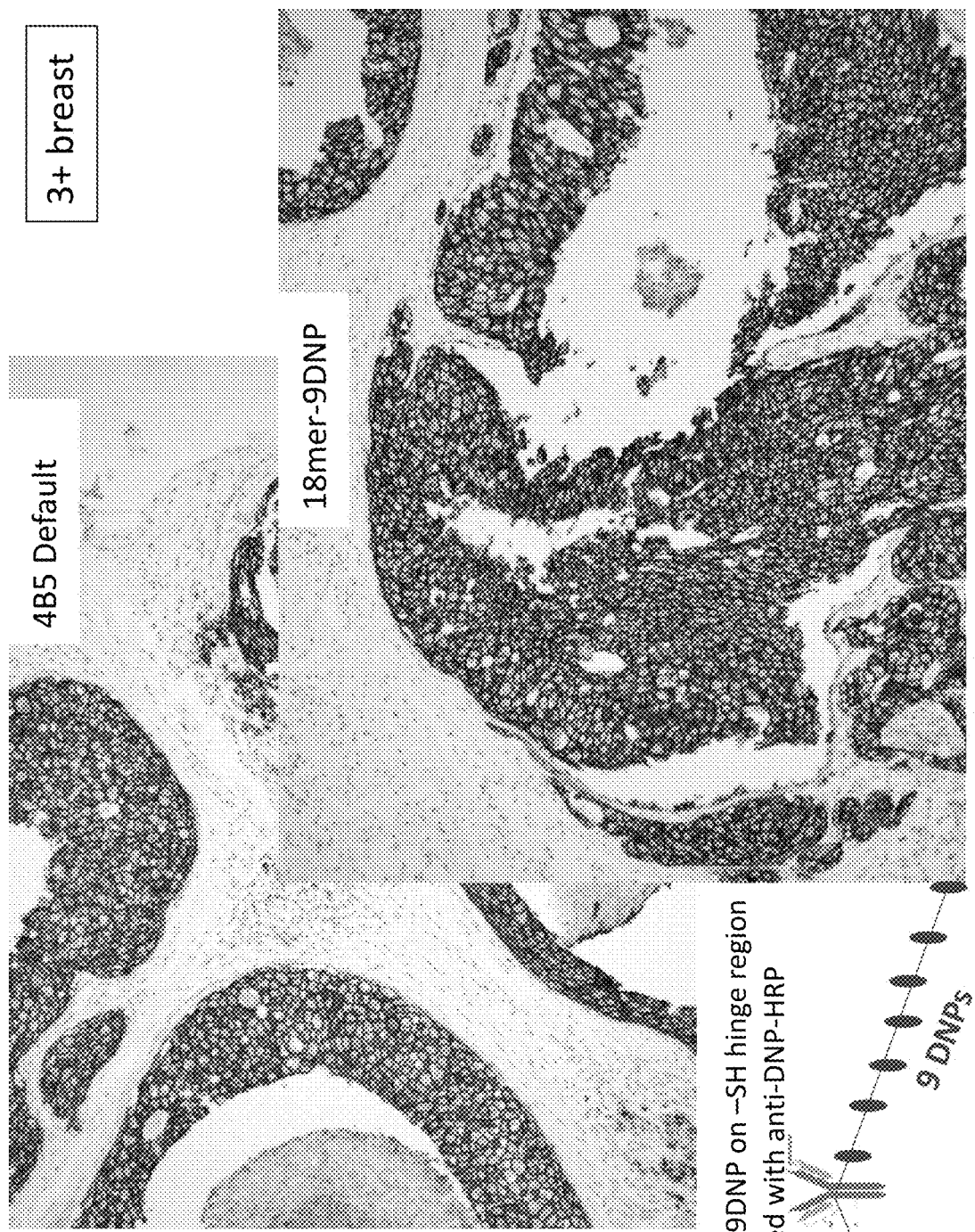
Figure 11:
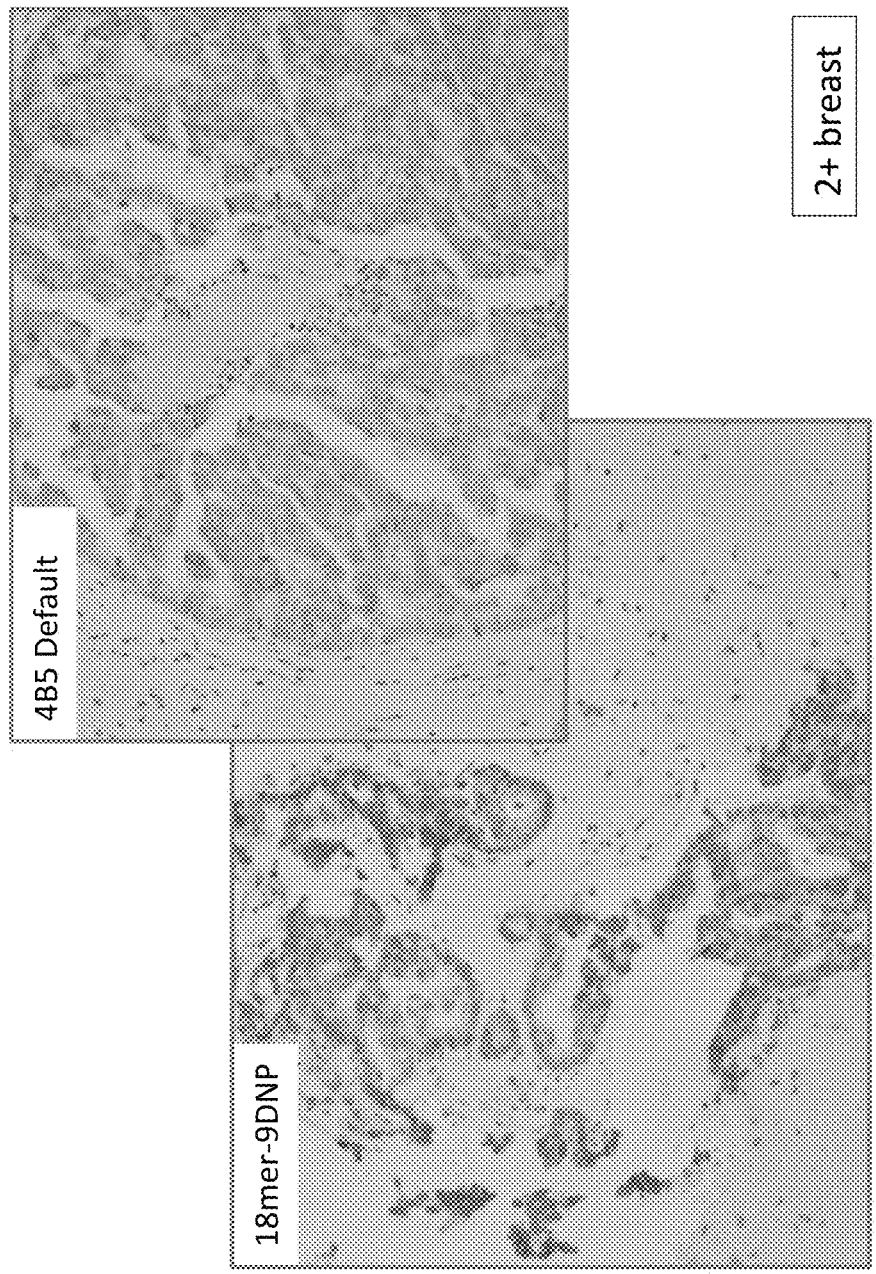
Figure 12:
Figure 12:
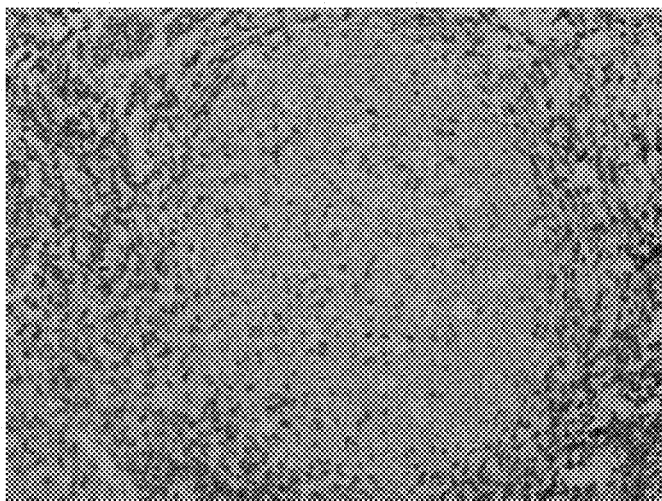
Figure 12:
Figure 13:
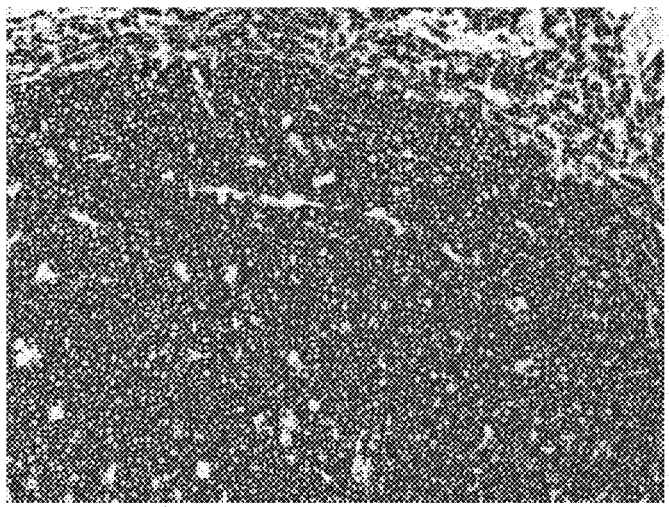
Figure 13:
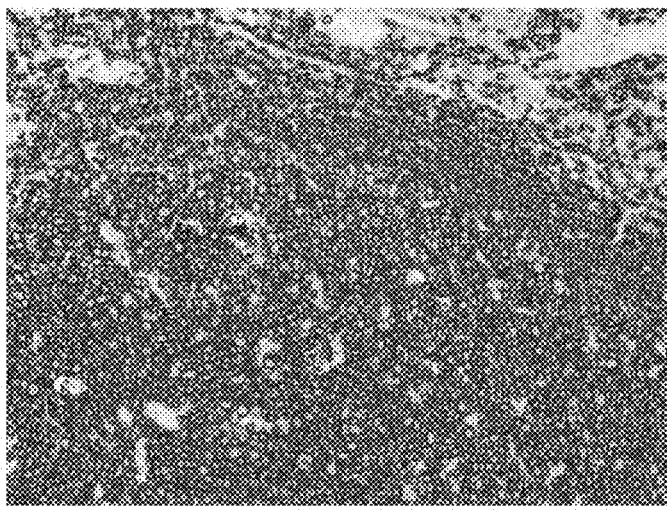
Figure 13:
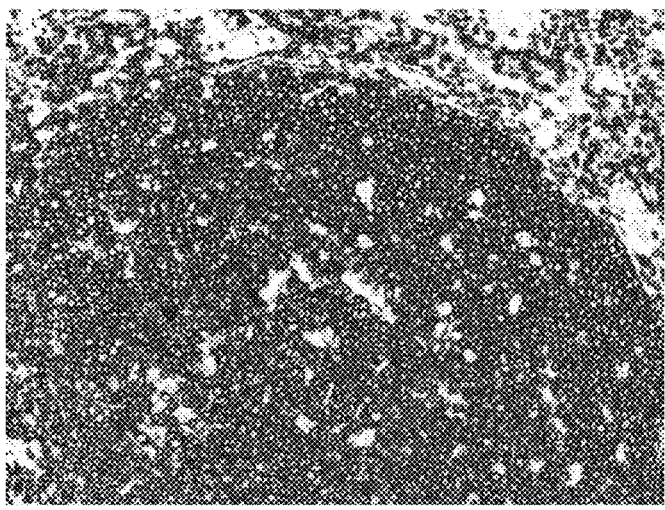
Figure 14:
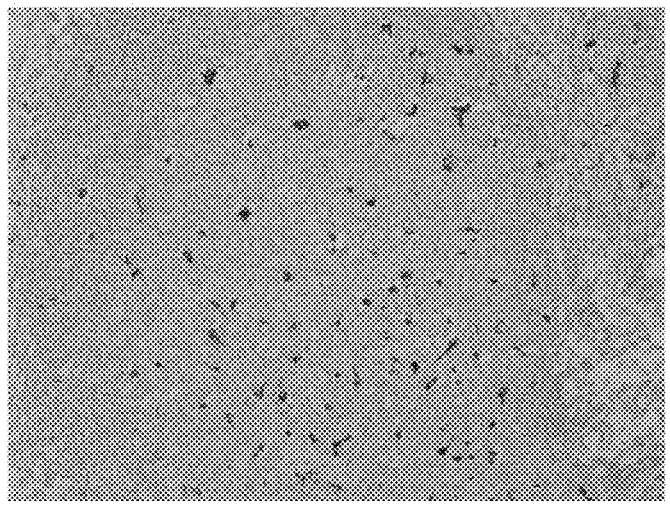
Figure 14:
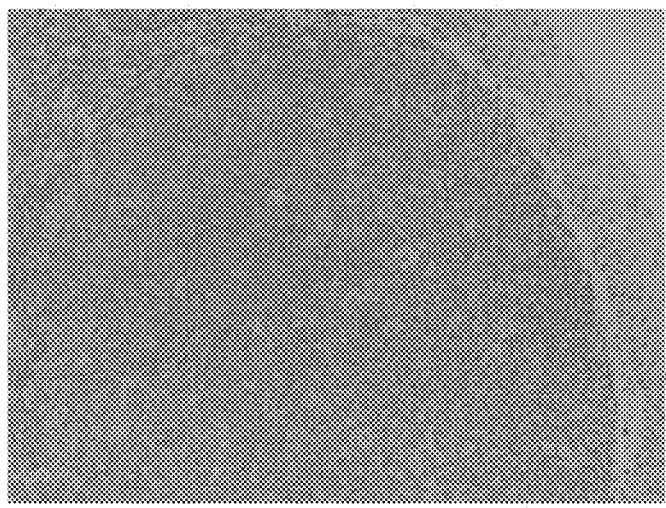
Figure 14:
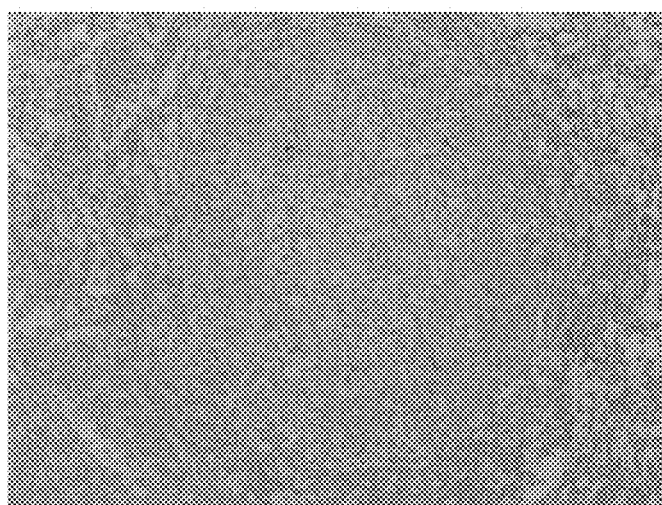

The HER2 4B5-4DNP randomly labeled with polymers of Formula Xd stained stronger than the native HER2 4B5 antibody (see FIGS. 10 and 11). Without wishing to be bound by any particular theory, it is believed that the labeled antibody retained its affinity because of the low-degree labeling to the disulfide bond in the hinge region which is away from CDR. Since the same anti-DNP detection system is used in Examples 1 and 2, Applicants believe that the stronger staining by the HER2 antibody labeled with the nucleotide polymer is not due to the difference of the anti-rabbit antibody (for native HER2 antibody) and anti-DNP antibody (for HER2 antibody labeled with nucleotide polymer).

Example 3

Staining for CD3, CD8, CD20, CD68 and FoxP3 protein with native anti-CD3, CD8, CD20, CD68 and FoxP3 rabbit antibody and the rabbit antibodies labeled with polymers of Formula (Xe) on thiol residues at the hinge region were performed on a BenchMark ULTRA automated stainer. Briefly, approximately 4 mm-thick-unstained tonsil sections were cut onto SuperFrost Plus glass slides. The BenchMark ULTRA automated stainer includes online deparaffinization at about 72° C. and antigen retrieval (about 95° C. for about 64 min). The native rabbit antibodies (about 1 ug/ml) or the respective antibody conjugates (about 1 ug/ml) were incubated for about 16 minutes at about 3TC. For the native rabbit antibodies, antigen detection was performed with about 25 ug/ml of goat anti-rabbit antibody labeled with horseradish peroxidase (HRP) (prepared from ULTRAVIEW UNIVERSAL DAB DETECTION KIT, 760-500). For the respective antibody conjugates comprising polymers of Formula (Xe), about 1.0 mg/ml of fish DNA was bulked as blocking reagent. Antigen detection was performed with about 20 ug/ml of a mouse anti-DNP-HRP antibody (prepared from DISCOVERY anti-DNP HRP Multimer RUO, 760-4821) Diaminobenzidine (DAB) was used as the chromogen, and Hematoxylin was used as the counterstain.

CD3, CD20, CD68 and FoxP3 antibodies coupled to the polymers of Formula (Xe) all worked with anti-DNP-HRP and uV GaR-HRP detection. The similar staining with the anti-DNP antibody to that with anti-rabbit antibody suggests the major portion is conjugated antibody-polymers of Formula (Xe) complex, no the unconjugated antibody. Without the optimization of anti-DNP detection, CD3 and CD20 with anti-DNP staining was close to native control staining, while FoxP3 and CD68 with anti-DNP staining was weaker than native control.

Example 4

This example concerns detecting tissue epitopes, such as Ki-67 on tonsil, using quantum dots to recognize a secondary antibody associated with a polyhaptenylated oligonucleotide-primary antibody conjugate using a Ventana Medical Systems, Inc. Benchmark Instrument. A paraffin coated tissue on a slide is heated to 75° C. for 4 minutes and treated twice with EZPrep volume adjust (VMSI) at 75° C. before application of the liquid cover slip (VMSI) with EZPrep volume adjust. After 4 minutes at 75° C., the slide is rinsed and EZPrep volume adjust is added along with liquid cover slip to deparraffinize the tissue at 76° C. for 4 minutes. The slide is cooled to 40° C. and rinsed three times before the addition of an anti-Ki67 15 (100 µL, VMS') antibody-haptenized polymer conjugate (e.g. Formula (I), followed by liquid cover slip and incubation at 40° C. for 16 minutes. After rinsing the slide, the tissue is treated with antihapten antibody (100 µL), followed by liquid cover slip and incubation at 40° C. for 8 minutes. The slide is rinsed twice with buffer followed by the application of liquid cover slip. The slide is rinsed three times with buffer and treated to a detergent wash before manual application of a cover slip to the slide, after which the slide is viewed through a microscope.

Example 5

This example concerns detecting tissue epitopes, particularly Ki-67 on tonsil, using either chromogenic staining (i.e. HRP-mediated deposition of DAB) or Qdots to recognize an antibody conjugated with a polyhaptenylated polymer. The following is the adapted procedure from the Ventana Benchmark Instrument. Paraffin-coated tissue on the slide is heated to 75° C. for 4 minutes and treated twice with EZPrep volume adjust (VMSI) at 75° C. before application of the liquid cover slip (VMSI) with EZPrep volume adjust. After 4 minutes at 75° C., the slide is rinsed and EZPrep volume adjust is added along with liquid cover slip to deparaffin the tissue at 76° C. for 4 minutes. The slide is cooled to 40° C. and rinsed three times before the addition of a mouse anti-Ki67 (100 µL, VMSI) antibody followed by liquid cover slip and incubation at 40° C. for 16 minutes. After rinsing the slide, the tissue is treated with a goat anti-mouse-polymer-DNP antibody (100 µl) followed by liquid cover slip and incubation at 40° C. for 8 minutes. The slide is rinsed twice with buffer followed by the application of liquid cover slip and the addition of 655 nm QDot:anti-DNP MAb conjugate (100 µL, 20 nmol) and incubation at 37° C. for 16 minutes. The slide is rinsed three times with buffer 20 and treated to a detergent wash before manual application of a cover slip to the slide, after which the slide is viewed through a microscope.

Example 6

This example concerns evaluating horseradish peroxidase-antibody conjugates, particularly evaluation of HPV in different tissues using Fc-conjugated polymer-biotin conjugates for SISH detection. The following is an adapted procedure from the Ventana Benchmark Instrument. A paraffin coated tissue on the slide is heated to 75° C. for 4 minutes and treated twice with EZPrep volume adjust (VMS1) at 75° C. before application of a liquid cover slip (VMSI) with EZPrep volume adjust. After 4 minutes at 75° C., the slide is rinsed and EZPrep volume adjust is added, along with liquid cover slip to deparaffin the tissue at 76° C. for 4 minutes. Cell Conditioner #2 (VMSI) is added, the slide is warmed to 90° C., and incubated for 8 minutes. This is followed by another application of Cell Conditioner #2 and incubation at 90° C. for 12 minutes. The slide is rinsed with Reaction Buffer (VMSI), cooled to 37° C. and ISH-Protease 3 (100 µL, VMSI) is added. After an incubation of 4 minutes, the slide is rinsed three times before the application of iView+HybReady (100 µL, VMSI), which is incubated for 4 minutes. Addition of HPV probe (200 µL VMSI) is followed by an incubation of 4 minutes at 37° C., 12 minutes at 95° C. and 124 minutes at 52° C. The slide is then rinsed twice and warmed to 72° C. This last step is repeated two more times before cooling the slide down to 37° C. and adding iView+Anti-DNP (100 µL, VMSI). The primary antibody is incubated for 20 minutes and the slide is then rinsed twice before the manual addition of an oligonucleotide-biotinylated secondary (e.g. goat anti-rabbit, 100 µL, 10 µg/ml). Incubation of the secondary is for 8 minutes and the slide is rinsed twice. Rabbit anti-biotin antibody is then applied (100 µL) and incubation occurs for another 20 minutes. After two more rinse steps, an HRP multimer is applied (100 µL, 10 µg/ml) and incubated for 8 minutes. Four more rinse steps are followed by the application of the SISH Chromagen A (100 µL VMSI) with a 4-minute incubation, SISH Chromagen B (100 µL, VMSI) with a 4-minute incubation, and SISH Chromagen C (100 µL, VMSI) with a 4-minute incubation. The slide is rinsed three times, and Hematoxylin II (100 µL, VMSI) is added. After incubation with the counterstain for 4 minutes, the slide is rinsed and Bluing Reagent (100 µL, VMSI) is applied and incubated for 4 minutes. The slide is then rinsed three more times and taken off of the instrument. The slide is treated to a detergent wash before dehydration with ethanol, acetone and xylene and subsequent application of a cover slip to the slide, after which the slide is viewed through a microscope.

The invention claimed is:

1. A polymer of Formula (V),

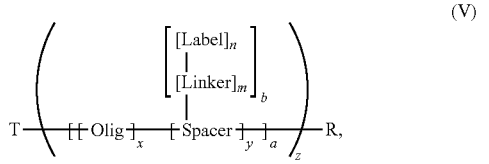

wherein
'Olig' is a single-stranded oligonucleotide sequence having between 1 and about 50 nucleotides, wherein the oligonucleotide sequence has a $T_m$ of less than 70° C.;
'Spacer' is a saturated straight chain aliphatic group having between 4 and 32 carbon atoms, wherein the aliphatic group is unbranched and unsubstituted, and optionally includes one or more oxygen atoms;
'Linker' is a saturated straight chain aliphatic group having between 4 and 18 carbon atoms, wherein the aliphatic group is unbranched and unsubstituted, and optionally includes one or more oxygen atoms;
'Label' is selected from the group consisting of haptens, chromogens, and enzymes;
R is H, a hydroxyl group, an amino group, a carbonyl group, a phosphate group, a phosphodiester group, or a cation;
T is a group having a terminal reactive moiety;
x is 1 or 2;
y is 1, or 2;
z is an integer ranging from 2 to 18;
m is 1, or 2;
n is 1 or 2;
a is an integer ranging from 1 to 8;
b is 1 or 2; and
wherein any of the 'Olig', 'Spacer,' 'Linker' or 'Label' may be bonded directly to each other or through an optional group; and
wherein at least one of the 'Spacer' and the 'Linker' comprises a moiety having Formula (IX):

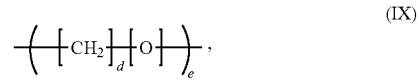

where d and e are each independently an integer ranging from 1 to 32,
wherein the 'Label' is selected from the group consisting of a di-nitrophenyl, biotin, digoxigenin, fluorescein, a fluorescein derivative, a rhodamine, an oxazole, a pyrazole, a thiazole, a nitroaryl, a benzofuran, a triterpene, a urea, a thiourea, a rotenoid, a coumarin, a cyclolignan, 5-nitro-3-pyrazole carbamide, 2-(3,4-dimethoxyphenyl)quinoline-4-carboxylic acid), 3-hydroxy-2-quinoxalinecarbamide, 2,1,3-benzoxadiazole-5-carbamide, and 2-acetamido-4-methyl-5-thiazolesulfonamide.

2. The polymer of claim 1, wherein the 'Olig' comprises between 2 and about 50 nucleotides.

3. The polymer of claim 1, wherein the 'Olig' comprises between 2 and about 24 nucleotides.

4. The polymer of claim 1, wherein the 'Olig' comprises between 4 and about 24 nucleotides; x is 1; y is 1; and a is 1 or 2.

5. The polymer of claim 1, wherein d ranges from 1 to 4; and e ranges from 2 to 8.

6. The polymer of claim 1, wherein the 'Linker' includes a group derived from a poly(alkylene)glycol.

7. The polymer of claim 1, wherein the 'Label' is selected from the group consisting of di-nitrophenyl, biotin, digoxigenin, fluorescein or a derivative thereof, or rhodamine.

8. The polymer of claim 1, wherein the 'Label' is selected from the group consisting of oxazoles, pyrazoles, thiazoles, nitroaryls, benzofurans, triterpenes, ureas, thioureas, rotenoids, coumarins, or cyclolignans.

9. The polymer of claim 1, wherein the 'Label' is selected from the group consisting of 5-nitro-3-pyrazole carbamide, 2-(3,4-dimethoxyphenyl)quinoline-4-carboxylic acid), 3-hydroxy-2-quinoxalinecarbamide, 2,1,3-benzoxadiazole-5-carbamide, and 2-acetamido-4-methyl-5-thiazolesulfonamide.

10. The polymer of claim 1, wherein x is 1; y is 1 or 2; a is 1 or 2; and z ranges from between 3 to 18.

11. The polymer of claim 10, wherein x is 1; y is 1; a is 1 or 2; and z ranges from between 3 to 9.

12. The polymer of claim 11, wherein a is 2; and m, n, and b are 1.

13. The polymer of claim 12, wherein the 'Label' is fluorescein or a fluorescein derivative.

14. The polymer of claim 13, wherein 'Olig' comprises between 4 and 18 nucleotides; and wherein 'Linker' comprises between 4 and 12 carbon atoms.

15. The polymer of claim 11, wherein a is 1; and m, n, and b are 1.

16. The polymer of claim 15, wherein the 'Label' is di-nitrophenyl.

17. The polymer of claim 16, wherein 'Olig' comprises between 4 and 18 nucleotides; and wherein 'Linker' comprises between 4 and 12 carbon atoms.

18. The polymer of claim 1, wherein a ratio of a:b is 2:1 or 3:1; and wherein a number of 'Label' groups present per polymer ranges from 3 to 9.

19. The polymer of claim 1, where the terminal reactive moiety of T is an amino group, a carboxyl group, or a sulfhydryl group.

20. The polymer of claim 1, wherein the polymer has the structure of Formula (VIa):

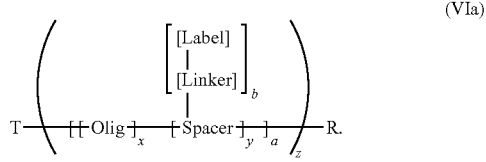

(VIa)

21. The polymer of claim 1, wherein the polymer has the structure of Formula (VIb):

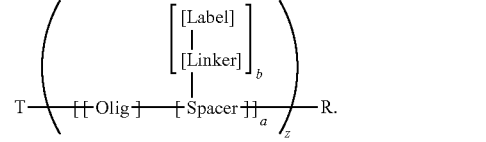

(VIb)

22. The polymer of claim 1, wherein the polymer has the structure of Formula (VIc):

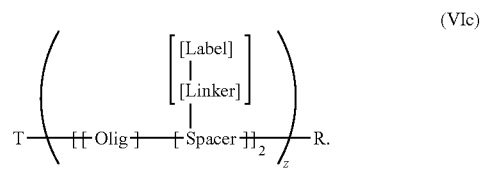

(VIc)

23. A polymer of Formula (V),

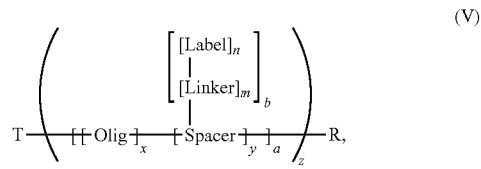

(V)

wherein

'Olig' is an oligonucleotide sequence having between 1 and about 50 nucleotides, wherein the oligonucleotide sequence has a $T_m$ of less than 70° C.;

'Spacer' is a saturated straight chain aliphatic group having between 4 and 32 carbon atoms, wherein the aliphatic group is unbranched and unsubstituted, and optionally includes one or more oxygen atoms;

'Linker' is a saturated straight chain aliphatic group having between 4 and 18 carbon atoms, wherein the aliphatic group is unbranched and unsubstituted, and optionally includes one or more oxygen atoms;

'Label' is selected from the group consisting of haptens, fluorophores, chromogens, enzymes and quantum dots;

R is H, a hydroxyl group, an amino group, a carbonyl group, a phosphate group, a phosphodiester group, or a cation T is a group having a terminal reactive moiety;

x is 1 or 2;

y is 1, or 2;

z is an integer ranging from 2 to 18;

m is 1, or 2;

n is 1 or 2;

a is an integer ranging from 1 to 8;

b is 1 or 2; and wherein any of the 'Olig', 'Spacer,' 'Linker' or 'Label' may be bonded directly to each other or through an optional group, and wherein 'Spacer' and 'Linker' are different; and wherein at least one of the 'Spacer' or the 'Linker' comprises a moiety having Formula (IX):

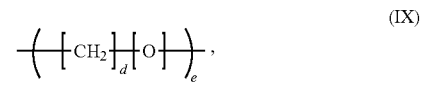

(IX)

where each d is independently an integer ranging from 1 to 32, and where e is an integer ranging from 2 to 32; and where the haptens are selected from the group consisting of pyrazoles, nitrophenyl compounds, benzofurazans, triterpenes, ureas, thioureas, rotenone, rotenone derivatives, oxazole s, thiazoles, coumarins, coumarin derivatives, nitroaryls, triterpenes, and cyclolignans.

24. The polymer of claim 23, wherein both the 'Spacer' and the 'Linker' comprise a moiety having Formula (IX):

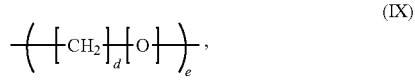

Wherein each d is independently an integer ranging from 1 to 32, and wherein e is an integer ranging from 2 to 32.

25. The polymer of claim 1, wherein both the 'Spacer' and the 'Linker' comprise a moiety having Formula (IX):

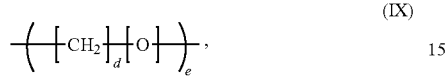

where d and e are each independently an integer ranging from 1 to 32.

26. A polymer of Formula (V),

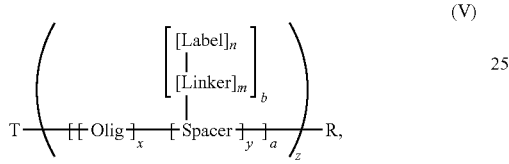

wherein

'Olig' is a single-stranded oligonucleotide sequence having between 1 and about 50 nucleotides, wherein the oligonucleotide sequence has a $T_m$ of less than 70° C.;

'Spacer' is a saturated straight chain aliphatic group having between 4 and 32 carbon atoms, wherein the aliphatic group is unbranched and unsubstituted, and optionally includes one or more oxygen atoms;

'Linker' is a saturated straight chain aliphatic group having between 4 and 18 carbon atoms, wherein the aliphatic group is unbranched and unsubstituted, and optionally includes one or more oxygen atoms;

'Label' is a fluorophore or a hapten;

R is H, a hydroxyl group, an amino group, a carbonyl group, a phosphate group, a phosphodiester group, or a cation;

T is a group having a terminal reactive moiety;

x is 1 or 2;

y is 1, or 2;

z is an integer ranging from 3 to 6;

m is 1, or 2;

n is 1 or 2;

a is an integer ranging from 1 to 8;

b is 1 or 2; and wherein any of the 'Olig', 'Spacer,' 'Linker' or 'Label' may be bonded directly to each other or through an optional group; and wherein at least one of the 'Spacer' and the 'Linker' comprises a moiety having Formula (IX):

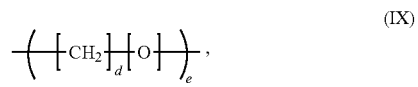

where d and e are each independently an integer ranging from 1 to 32.

27. The polymer of claim 26, wherein both the 'Spacer' and the 'Linker' comprise a moiety having Formula (IX):

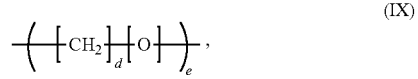

where d and e are each independently an integer ranging from 1 to 32.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
tatttttatt tttattttta tttt                                          24

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
tatttttatt tttattttta tttttatttt                                    30

<210> SEQ ID NO 3
<211> LENGTH: 42
<212> TYPE: DNA
<213> ORGANISM: Artificial Sequence
<220> FEATURE:
<223> OTHER INFORMATION: Synthetic

<400> SEQUENCE: 3
tatttttatt tttattttta tttttatttt tatttttatt tt                      42

<210> SEQ ID NO 4
<211> LENGTH: 54
<212> TYPE: DNA
<213> ORGANISM: Artificial Sequence
<220> FEATURE:
<223> OTHER INFORMATION: Synthetic

<400> SEQUENCE: 4
tatttttatt tttattttta tttttatttt tatttttatt tttattttta tttt         54

<210> SEQ ID NO 5
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' (AminoC6)
<220> FEATURE:
<221> NAME/KEY: misc_feature
<222> LOCATION: (6)..(7)
<223> OTHER INFORMATION: site of DNP hapten
<220> FEATURE:
<221> NAME/KEY: misc_feature
<222> LOCATION: (12)..(13)
<223> OTHER INFORMATION: site of DNP hapten
<220> FEATURE:
<221> NAME/KEY: misc_feature
<222> LOCATION: (18)..(19)
<223> OTHER INFORMATION: site of DNP hapten

<400> SEQUENCE: 5
tatttttatt tttattttt                                                19

```
<210> SEQ ID NO 6
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' (AminoC6)
<220> FEATURE:
<221> NAME/KEY: misc_feature
<222> LOCATION: (6)..(7)
<223> OTHER INFORMATION: site of DNP hapten
<220> FEATURE:
<221> NAME/KEY: misc_feature
<222> LOCATION: (12)..(13)
<223> OTHER INFORMATION: site of DNP hapten
<220> FEATURE:
<221> NAME/KEY: misc_feature
<222> LOCATION: (18)..(19)
<223> OTHER INFORMATION: site of DNP hapten
<220> FEATURE:
<221> NAME/KEY: misc_feature
<222> LOCATION: (24)..(25)
<223> OTHER INFORMATION: site of DNP hapten

<400> SEQUENCE: 6
tattttattt tttattttta ttttt                                    25

<210> SEQ ID NO 7
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' (AminoC6)
<220> FEATURE:
<221> NAME/KEY: misc_feature
<222> LOCATION: (6)..(7)
<223> OTHER INFORMATION: site of DNP hapten
<220> FEATURE:
<221> NAME/KEY: misc_feature
<222> LOCATION: (12)..(13)
<223> OTHER INFORMATION: site of DNP hapten
<220> FEATURE:
<221> NAME/KEY: misc_feature
<222> LOCATION: (18)..(19)
<223> OTHER INFORMATION: site of DNP hapten
<220> FEATURE:
<221> NAME/KEY: misc_feature
<222> LOCATION: (24)..(25)
<223> OTHER INFORMATION: site of DNP hapten
<220> FEATURE:
<221> NAME/KEY: misc_feature
<222> LOCATION: (30)..(31)
<223> OTHER INFORMATION: site of DNP hapten

<400> SEQUENCE: 7
tattttattt tttattttta ttttattttt t                             31

<210> SEQ ID NO 8
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' (AminoC6)
<220> FEATURE:
<221> NAME/KEY: misc_feature
<222> LOCATION: (6)..(7)
<223> OTHER INFORMATION: site of DNP hapten
```

```
<220> FEATURE:
<221> NAME/KEY: misc_feature
<222> LOCATION: (12)..(13)
<223> OTHER INFORMATION: site of DNP hapten
<220> FEATURE:
<221> NAME/KEY: misc_feature
<222> LOCATION: (18)..(19)
<223> OTHER INFORMATION: site of DNP hapten
<220> FEATURE:
<221> NAME/KEY: misc_feature
<222> LOCATION: (24)..(25)
<223> OTHER INFORMATION: site of DNP hapten
<220> FEATURE:
<221> NAME/KEY: misc_feature
<222> LOCATION: (30)..(31)
<223> OTHER INFORMATION: site of DNP hapten
<220> FEATURE:
<221> NAME/KEY: misc_feature
<222> LOCATION: (36)..(37)
<223> OTHER INFORMATION: site of DNP hapten
<220> FEATURE:
<221> NAME/KEY: misc_feature
<222> LOCATION: (42)..(43)
<223> OTHER INFORMATION: site of DNP hapten
<220> FEATURE:
<221> NAME/KEY: misc_feature
<222> LOCATION: (48)..(49)
<223> OTHER INFORMATION: site of DNP hapten
<220> FEATURE:
<221> NAME/KEY: misc_feature
<222> LOCATION: (54)..(55)
<223> OTHER INFORMATION: site of DNP hapten

<400> SEQUENCE: 8 tattttatt tttatttta tttttatttt tattttatt tttatttta ttttt         55
```